United States Patent
Dufrane

(10) Patent No.: US 11,203,785 B2
(45) Date of Patent: Dec. 21, 2021

(54) METHODS FOR ASSESSING THE PURITY OF A MESENCHYMAL STEM CELLS PREPARATION

(71) Applicants: UNIVERSITÉ CATHOLIQUE DE LOUVAIN, Louvain la Neuve (BE); CLINIQUES UNIVERSITAIRES SAINT-LUC, Brussels (BE); NOVADIP BIOSCIENCES SA, Mont-Saint-Guibert (BE)

(72) Inventor: Denis Dufrane, Wavre (BE)

(73) Assignees: UNIVERSITÉ CATHOLIQUE DE LOUVAIN, Louvain-la-Neuve (BE); CLINIQUES UNIVERSITAIRES SAINT-LUC, Brussels (BE); NOVADIP BIOSCIENCES SA, Mont-Saint (BE)

( * ) Notice: Subject to any disclaimer, the term of this patent is extended or adjusted under 35 U.S.C. 154(b) by 0 days.

(21) Appl. No.: 15/571,461

(22) PCT Filed: May 9, 2016

(86) PCT No.: PCT/EP2016/060351
§ 371 (c)(1),
(2) Date: Nov. 2, 2017

(87) PCT Pub. No.: WO2016/180788
PCT Pub. Date: Nov. 17, 2016

(65) Prior Publication Data
US 2018/0135124 A1    May 17, 2018

Related U.S. Application Data

(60) Provisional application No. 62/158,875, filed on May 8, 2015.

(30) Foreign Application Priority Data

Jul. 31, 2015  (EP) .................................... 15179417

(51) Int. Cl.
*C12Q 1/6881* (2018.01)
*C12N 5/0775* (2010.01)
*G01N 33/74* (2006.01)
*G01N 33/53* (2006.01)
*G01N 33/50* (2006.01)

(52) U.S. Cl.
CPC ......... *C12Q 1/6881* (2013.01); *C12N 5/0662* (2013.01); *C12N 5/0667* (2013.01); *G01N 33/5005* (2013.01); *G01N 33/53* (2013.01); *G01N 33/74* (2013.01); *C12Q 2600/158* (2013.01); *G01N 2333/475* (2013.01)

(58) Field of Classification Search
None
See application file for complete search history.

(56) References Cited

U.S. PATENT DOCUMENTS

| | | | |
|---|---|---|---|
| 2001/0049139 A1 | 12/2001 | Lagasse | |
| 2010/0261202 A1* | 10/2010 | Kuwana | A61L 27/3834 435/7.21 |
| 2010/0304477 A1* | 12/2010 | Buscher | C12N 5/0657 435/325 |
| 2013/0251670 A1* | 9/2013 | Riordan | A61K 35/51 424/85.2 |
| 2014/0170122 A1 | 6/2014 | Shim | |

FOREIGN PATENT DOCUMENTS

| | | |
|---|---|---|
| EP | 2 460 876 A2 | 6/2012 |
| JP | 2013536855 | 9/2013 |
| JP | 2015077074 | 4/2015 |
| WO | 2014144392 | 9/2014 |

OTHER PUBLICATIONS

Alt et al. (2011) "Fibroblasts share mesenchymal phenotypes with stem cells, but lack their differentiation and colony-forming potential," Biol. Cell. 103(4):197-208.

Blasi et al. (2011) "Dermal fibroblasts display similar phenotypic and differentiation capacity to fat-derived mesenchymal stem cells, but differ in anti-inflammatory and angiogenic potential," Vasc. Cell. 3(1):5. pp. 1-14.

Bourin et al. (Apr. 6, 2013) Stromal cells from the adipose tissue-derived stromal vascular fraction and culture expanded adipose tissue-derived stromal/stem cells: a joint statement of the International Federation for Adipose Therapeutics and Science (IFATS) and the International Society for Cellular Therapy (ISCT), Cytotherapy. 15:641-648.

Dominici et al. (2006) "Minimal criteria for defining multipotent mesenchymal stromal cells. The International Society for Cellular Therapy position statement," Cytotherapy. 8(4):315-317.

Goodpaster et al. (2008) "An immunohistochemical method for identifying fibroblasts in formalin-fixed, paraffin-embedded tissue," Journal of Histochemistry & Cytochemistry 56(4):347-358.

Hematti (2012) "Mesenchymal stromal cells and fibroblasts: a case of mistaken identity?" Cytotherapy. 14:516-521.

Jaager et al. (2012) "RNA-seq analysis reveals different dynamics of differentiation of human dermis- and adipose-derived stromal stem cells," PLoS One 7(6):e38833.

Mishra et al. (2008) "Carcinoma-associated fibroblast-like differentiation of human mesenchymal stem cells," Cancer Res. 68(11):4331-4339.

(Continued)

*Primary Examiner* — Katherine D Salmon
(74) *Attorney, Agent, or Firm* — Lathrop GPM LLP; James H. Velema; Judith L. Stone-Hulslander

(57) ABSTRACT

The present invention relates to a method for assessing, evaluating and/or monitoring the purity of a mesenchymal stem cells preparation, in particular of an adipose stem cells preparation, comprising measuring the expression level of at least one growth factor.

11 Claims, 7 Drawing Sheets

(56) References Cited

OTHER PUBLICATIONS

Pilling et al. (2010) "Identification of markers that distinguish monocyte-derived fibrocytes from monocytes, macrophages, and fibroblasts," PLoS One 4(10):e7475. pp. 1-18.
Qu et al. (2007) "Osteogenic and adipogenic potential of porcine adipose mesenchymal stem cells," In Vitro Cell Dev Biol Anim. 43:95-100.
Zych et al. (Nov. 15, 2014) "Polysome profiling shows the identity of human adipose-derived stromal/stem cells in detail and clearly distinguishes them from dermal fibroblasts," Stem Cell Develop. 23(22):2791-2802.
International Search Report with Written Opinion corresponding to International Patent Application No. PCT/EP2016/060351, dated Jul. 15, 2016.

* cited by examiner

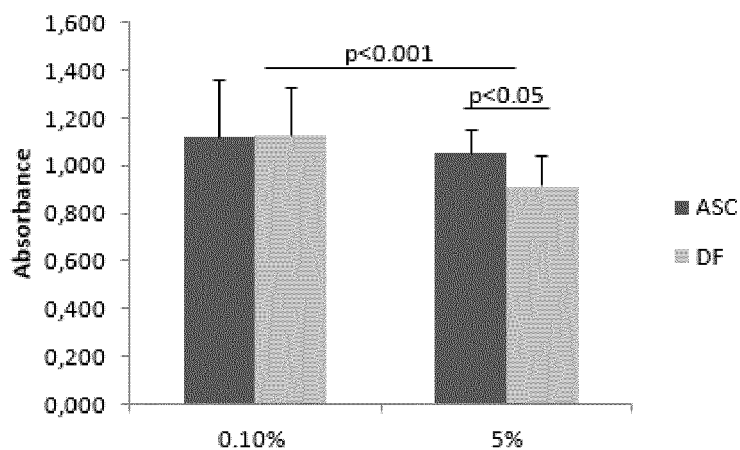
FIG. 3
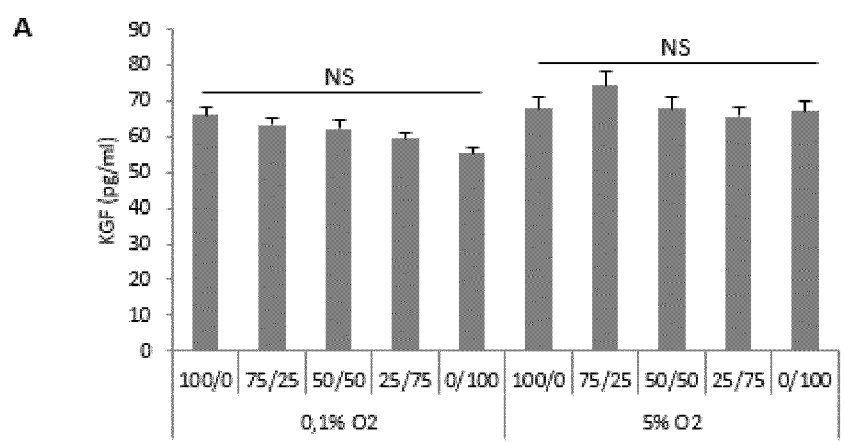
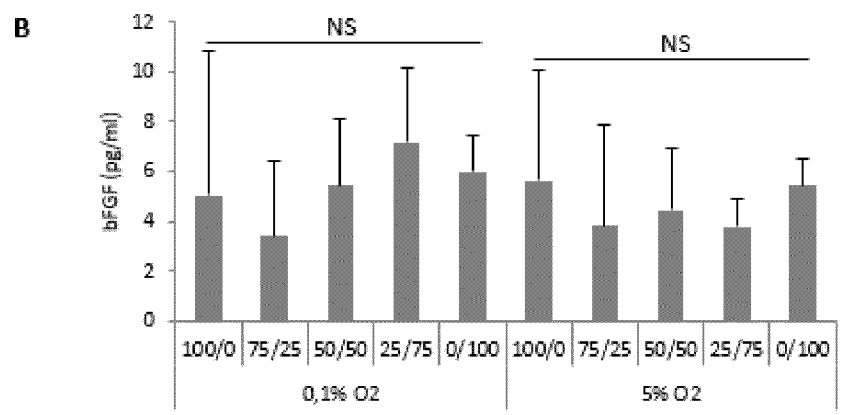
FIG. 4A-B

FIG. 4C-D

METHODS FOR ASSESSING THE PURITY OF A MESENCHYMAL STEM CELLS PREPARATION

RELATED APPLICATIONS

This application is a 35 U.S.C. § 371 filing of International Patent Application No. PCT/EP2016/060351, filed May 9, 2016, which claims priority to U.S. Provisional Patent Application Ser. No. 62/158,875, filed May 8, 2015, and European Patent Application No. 15179417.9, filed Jul. 31, 2015. Each of the aforementioned applications is incorporated herein by reference in its entirety.

FIELD OF INVENTION

The present invention relates to methods for assessing the purity of a cell preparation, in particular of a mesenchymal stem cells preparation. In particular, the present invention relates to growth factors as biomarker of the purity of a mesenchymal stem cells preparation.

BACKGROUND OF INVENTION

The use of stem cell-based therapies for the repair and regeneration of various tissues and organs offers alternative therapeutic solutions for a number of diseases. Mesenchymal stem cells (MSC) are plastic-adherent stromal cells characterized by their ability to differentiate into mesenchymal tissues such as bone, cartilage and fat. Because of these properties, MSC seem to be an ideal population of stem cells for practical regenerative medicine. One of the richest sources of MSC is adipose tissue and adipose-tissue derived stem cells (ASC) are widely investigated for development of new therapies in the field of regenerative medicine (such as, for example, for wound healing, bone/cartilage regeneration, Crohn's disease, . . . ).

Cell therapy products must be manufactured following the "Good Manufacturing Practice" recommendations which required a purity analysis of the final cellular products. However, fibroblasts may be common cell contaminants that affect the purity of mesenchymal stem cell preparations. Currently, cell therapy products remain non-characterized in term of cellular purity for fibroblastic cells. Indeed, current defined criteria for mesenchymal stem cells, including ASC, characterization are (i) plastic adherence for cell spreading and proliferation; (ii) surface markers profile (CD44+, CD45−, CD73+, CD90+, CD105+); and (iii) differentiation capacity toward adipose/osteogenic/chondrogenic lineages. However, mesenchymal stem cells and fibroblasts are considered nowadays as a subfamily without any capacities to differentiate according to these criteria (Hematti, Cytotherapy, 2012; 14:516-521). Fibroblasts are ubiquitous cells, present in variable tissues (dermis, adipose tissue, muscle . . . ). They are also plastic-adherent, express the similar surface marker phenotype as MSC and have the capacity to differentiate towards the mesenchymal lineages when cultivated in specific media.

Few studies relate to the identification of fibroblasts from other cells. Pilling et al. discloses the identification of markers that discriminate between human peripheral blood monocytes, tissue macrophages, fibrocytes and fibroblasts (PLoS One. 2009, 4(10):e7475). However mesenchymal stem cells are not included in this study. Moreover Goodpaster et al. describes that fibroblasts may be positively identified by the TE-7 antibody which specifically recognizes growing and quiescent fibroblasts in formalin-fixed, paraffin-embedded tissue samples (Journal of Histochemistry & Cytochemistry. 2008, 56(4):347-358). Nevertheless the TE-7 antibody was not tested on mesenchymal stem cells.

Accordingly, there is currently no quantitative and objective method to distinguish MSC from fibroblasts. Fibroblasts, however, are associated with cancer cells at all stages of cancer progression. A cell therapy product comprising fibroblasts is thus potentially carcinogenic. It therefore exists a need of tools to assess the purity of an MSC preparation with respect to fibroblastic contamination, in particular in context of cell therapy products preparation.

The inventors herein surprisingly demonstrate that mesenchymal stem cells and fibroblasts can be differentiated according to their capacity to secrete factors such as SDF-1α and VEGF.

Therefore, the present invention relates to a method for assessing the presence of fibroblasts in a preparation of mesenchymal stem cells, e.g. a composition comprising cells, and for quantifying the purity of such a preparation.

SUMMARY

This invention relates to an in vitro method for assessing, evaluating and/or monitoring the purity of a cell preparation comprising mesenchymal stem cells (MSC), wherein said method comprises measuring the expression level of at least one growth factor expressed by said cell preparation, wherein said at least one growth factor is SDF-1α and/or VEGF.

According to one embodiment, the method of the invention further comprises comparing the measured expression level with a reference expression level.

In one embodiment, the mesenchymal stem cells of the cell preparation of the invention are isolated from tissues selected from the group comprising adipose tissue, bone marrow, umbilical cord blood, amniotic fluid, Wharton's jelly, placenta, peripheral blood, fallopian tube, corneal stroma, lung, muscle and fetal liver. In a particular embodiment, the mesenchymal stem cells are adipose stem cells (ASC).

According to one embodiment, the expression level of at least one growth factor expressed by said cell preparation of the invention is assessed at the protein level, preferably by the detection and/or quantification of said at least one growth factor secreted in the cell culture supernatant. In a particular embodiment, the expression level is assessed at the RNA level, preferably by RT-PCR, RT-qPCR, Northern Blot and/or hybridization techniques.

According to one embodiment, the cell preparation of the invention is substantially pure when the SDF-1a expression level is of at most 100 pg/ml, preferably of at most 50, 40, 30, 25, 20, 19, 18, 17, 16, 15, 14, 13, 12, 11, 10, 9, 8, 7, 6, 5, 4, 3, 2 or 1 pg/ml.

According to another embodiment, the cell preparation of the invention is substantially pure when the SDF-1a expression level is of at most 100 pg/ml, preferably of at most 50, 40, 30, 25, 20, 19, 18, 17, 16, 15, 14, 13, 12, 11, 10, 9, 8, 7, 6, 5, 4, 3, 2 or 1 pg/ml; and/or the VEGF expression level is of at least 200 pg/ml in the cell culture medium, preferably of at least 250, 260, 270, 280, 281, 282, 283, 284, 285, 286, 287, 288, 289 or 290 pg/ml; wherein said cell preparation is cultured in hypoxic conditions, preferably at about 0.1% $O_2$, and at high concentration of glucose, preferably at about 4.5 g/l of glucose, before measuring the expression level.

According to another embodiment, the cell preparation of the invention is substantially pure when the SDF-1α expression level is of at most 100 pg/ml, preferably of at most 50, 40, 30, 25, 20, 19, 18, 17, 16, 15, 14, 13, 12, 11, 10, 9, 8, 7, 6, 5, 4, 3, 2 or 1 pg/ml; and/or the VEGF expression level is of at least 90 pg/ml in the cell culture medium, preferably of at least 95, 100, 105, 110, 111, 112, 113, 114, 115, 116, 117, 118, 119 or 120 pg/ml, wherein said cell preparation is cultured at tissular oxygen tension, preferably at about 5% $O_2$, and at high concentration of glucose, preferably at about 4.5 g/l of glucose, before measuring the expression level.

In one embodiment, the method of the invention is for assessing the quality or purity of a cell preparation comprising mesenchymal stem cells (MSC), wherein said cell preparation comprising MSC is to be used as MSC-based cell therapy product in regenerative medicine.

This invention also relates to the use of a growth factor, preferably SDF-la and/or VEGF, as a biomarker of the quality of a cell preparation comprising mesenchymal stem cells (MSC), in particular of a cell preparation comprising MSC to be used as MSC-based cell therapy product in regenerative medicine.

Another object of the invention is a cell population identified by the in vitro method as described hereinabove.

This invention also relates to a substantially pure mesenchymal stem cells population, preferably an adipose stem cells population.

This invention also encompasses to a kit for implementing the in vitro method as described hereinabove, wherein said kit comprises means for determining or measuring the expression level of at least one growth factor, optionally further comprising the reference for comparing the expression level of said at least one growth factor.

Definitions

In the present invention, the following terms have the following meanings:

"Purity of a cell preparation" refers to the enrichment of cells of interest from a heterogeneous population (also called mixed population). In one embodiment, cells of the invention are mesenchymal stem cells, preferably adipose tissue mesenchymal stem cells. In one embodiment, the purity according to the invention is expressed in percentage of mesenchymal stem cells, preferably adipose tissue mesenchymal stem cells, from a mixed population comprising other cell types, preferably fibroblasts.

"Mesenchymal stem cells" or MSCs, are multipotent stem cells that can differentiate into a variety of cell types including: osteogenic, chondrogenic, adipogenic, myelosupportive stroma, myogenic, or neurogenic lineages. Mesenchymal stem cells can be isolated from tissues including, without limitation, adipose tissue, bone-marrow, umbilical cord tissue, amniotic fluid, Wharton's jelly, placenta, peripheral blood, fallopian tube, corneal stroma, lung, muscle, skin, bone, dental tissue, pre-menstrual fluid, foreskin and fetal liver, and the like.

"Adipose tissue" refers to any fat tissue. The adipose tissue may be brown, yellow or white adipose tissue. Preferably, the adipose tissue is subcutaneous white adipose tissue. Adipose tissue includes adipocytes and stroma. Adipose tissue may be found throughout the body of an animal. For example, in mammals, adipose tissue may be present in the omentum, bone marrow, subcutaneous space, fat pads (e.g., scapular or infrapatellar fat pads), and surrounding most organs. Cells obtained from adipose tissue may comprise a primary cell culture or a progenitor cell line. The adipose tissue may be from any organism having fat tissue.

"Adipose tissue-derived cell" refers to a cell that originates from adipose tissue. In particular, "adipose tissue mesenchymal stem cells" (ASC) refer to stromal cells that originate from adipose tissue which can serve as precursors to a variety of different cell types such as, but not limited to, adipocytes, osteocytes, chondrocytes.

"Growth factor" refers to any substance participating in the regulation of the cellular proliferation or differentiation.

"Tissular oxygen levels" refers to oxygen levels from about 3% to about 6%, preferably at an oxygen level of about 5%.

"Hypoxic environment" refers to oxygen levels from about 0% to about 1%, preferably at an oxygen level of about 0.1%.

"Normoglycemic conditions" refers to a concentration of glucose of from about 0.5 g/l to about 1.5 g/l, preferably at a concentration of glucose of about 1 g/l.

"Hyperglycaemic conditions" refers to a concentration of glucose from about 2 g/l to about 10 g/l, preferably from about 3 g/l to about 6 g/l, more preferably at a concentration of glucose of about 4.5 g/l.

"About" preceding a value means plus or less 10% of said value.

"Passaging", also known as subculture or splitting cells, refers to transferring a small number of cells into a new vessel when cells are at confluence or almost, to prolong the life and/or expand the number of cells in the culture. In one embodiment, the passage 0 (P0) is the point at which cells were initially placed in culture.

"Late passaged mesenchymal stem cell" refers to a cell exhibiting a less immunogenic characteristic when compared to an earlier passaged cell. The immunogenicity of a mesenchymal stem cell corresponds to the number of passages. Preferably, the cell has been passaged up to at least the fourth passage, more preferably, the cell has been passaged up to at least the sixth passage, and most preferably, the cell has been passaged up to at least the eight passage.

DETAILED DESCRIPTION

This invention relates to a method, preferably an in vitro method, for assessing, evaluating and/or monitoring the purity of a cell preparation comprising mesenchymal stem cells (MSC), e.g. a composition of cells comprising MSC, wherein said method comprises determining or measuring the expression level of at least one growth factor expressed by said cell preparation. In one embodiment, MSC are adipose tissue-derived mesenchymal stem cells (ASC).

In one embodiment, the method of the invention is for assessing the presence of fibroblasts in a cell preparation comprising mesenchymal stem cells. According to this embodiment, the method of the invention may thus correspond to a quality control method, aiming at checking, for example, the purity of a cell preparation comprising MSC with respect to fibroblastic contamination. Those MSC may be, for example, used for MSC-based cell therapy product.

In one embodiment, the method of the invention is for quantifying the purity of a cell preparation comprising mesenchymal stem cells. In one embodiment, the cell preparation is a heterogeneous preparation comprising mesenchymal stem cells and other cell types. In a particular embodiment, the cell preparation comprises mesenchymal stem cells and fibroblasts.

In one embodiment, the method of the invention is for quantifying the percentage of mesenchymal stem cells from a heterogeneous population comprising mesenchymal stem cells and other cell types, preferably fibroblasts.

The Applicant demonstrated that with progressive contaminations of MSC by fibroblasts, the expression level of growth factors tends to increase or decrease. Consequently, this invention demonstrates the capacity to discriminate MSC from fibroblasts, based on their specific growth factors expression. In particular, the discrimination may be based on their growth factors expression in specific conditions of oxygenation and/or glycemia.

Therefore, in one embodiment, the method of the invention is for assessing, evaluating and/or monitoring the purity of a cell preparation comprising MSC with respect to fibroblastic contamination, based on their specific growth factors expression.

Examples of growth factors include, but are not limited to, adipocytokines, angiopoietins, angiopoietin-like proteins and receptors thereof, chemokines and receptors thereof, common beta chain receptors, common gamma chain receptors, EGF, FGF, hedgehog proteins, IGF, interferons, interleukins and receptors, PDGF, TGF, TNF, VEGF, SDF-1 and Wnt.

In one embodiment, the method of the invention comprises measuring the expression level of SDF-1 (stromal cell-derived factor 1, also known as C—X—C motif chemokine 12 or CXCL12, Pre-B Cell Growth-stimulating Factor (PBSF), SCYB12 or TLSF) and/or VEGF (vascular endothelial growth factor). Preferably, SDF-1 is in the form of SDF-1α.

In one embodiment, the method according to the invention comprises measuring the expression level of SDF-1α. In another embodiment, the method according to the invention comprises measuring the expression level of VEGF. In another embodiment, the method according to the invention comprises measuring the expression level of SDF-1α and VEGF.

According to one embodiment, MSC are isolated from tissues selected from the group comprising adipose tissue, bone marrow, umbilical cord blood, Wharton's jelly (such as, for example, Wharton's jelly found within the umbilical cord), placenta, peripheral blood, fallopian tube, corneal stroma, lung, muscle skin, bone, dental tissue and fetal liver, or the like. In a particular embodiment, MSC are isolated from adipose tissue. In a preferred embodiment, MSC are adipose stem cells (ASC).

In one embodiment, MSC are isolated from any warm-blooded animal tissues, preferably from human tissues. In a particular embodiment, MSC are human ASC.

In one embodiment, the cells are cells in culture, preferably are cell lines and/or are derived from primary cells, i.e. cells isolated straight from the tissue. In one embodiment, the cells are recovered from a sample from an individual, obtained for example by biopsy. Preferably, the step of recovering the sample from an individual is not part of the method of the present invention.

Isolation of mesenchymal stem cells may be accomplished by any acceptable method known to one of ordinary skill in the art. Examples of methods for isolating MSC include, but are not limited to, digestion by collagenase, trypsinization, or explant culture.

In a particular embodiment, mesenchymal stem cells are isolated from adipose tissue by digestion of the tissue, for example by collagenase.

According to one embodiment of the invention, after isolation, the cell preparation comprising MSC is cultured in any culture medium designed to support the growth of the cells known to one of ordinary skill in the art. As used herein, such culture medium is called "proliferation medium" or "growth medium". Examples of growth medium include, without limitation, MEM, DMEM, IMDM, RPMI 1640, FGM or FGM-2, 199/109 medium, HamF10/HamF12 or McCoy's 5A, preferably DMEM or RPMI.

In one embodiment, the growth medium may further comprise any supplementary factors known by the person skilled in the art that may be used in cell culture. Examples of supplementary factors include, but are not limited to, FBS; glycine; amino acids, such as glutamine, asparagine, glutamic acid, aspartic acid, serine, proline or alanine, preferably the L-configuration of amino acids; and antibiotics, such as streptomycin or penicillin.

In a particular embodiment, the cell preparation comprising MSC is cultured in DMEM supplemented with fetal bovine serum, glutamine, preferably L-glutamine, and antibiotics such as penicillin, streptomycin and amphotericin B.

In one embodiment, the cell preparation comprising MSC may be contaminated by other types of cells, such as, for example, by fibroblasts. In a particular embodiment, the cell preparation comprising MSC is contaminated by fibroblasts.

In one embodiment, the cell preparation comprising MSC is cultured in growth medium up to at least 2 passages, preferably at least 3 passages, more preferably at least 4 passages. As used herein, the term "cultured up to at least 4 passages" means that the cell preparation is detached and transferred into a new vessel up to at least 4 times. In one embodiment, the mesenchymal stem cells of the cell preparation are late passaged mesenchymal stem cells.

For passaging cells, cells may be detached by one of several methods known to one of ordinary skill in the art, including trypsin treatment to break down the proteins responsible for surface adherence, chelating sodium ions with EDTA which disrupts some protein adherence mechanisms, or mechanical methods like repeated washing or use of a cell scraper. The detached cells are then resuspended in fresh medium.

In one embodiment, the cell preparation comprising MSC is cultured for at least 24 hours, preferably for at least 36, 48, 60 or 72 hours. In another embodiment, the cell preparation comprising MSC is cultured for at least 1 day, preferably for at least 2, 3, 4, 5, 6 or 7 days. In another embodiment, the cell preparation comprising MSC is cultured for at least 10, 15, 20, 25, 30, 35 or 40 days.

According to one embodiment, the cell preparation comprising MSC is cultured in standard culture conditions. As used herein, "standard culture conditions" means at a temperature of about 37° C., and at a tension of about 21% $O_2$ and of about 5% $CO_2$.

In one embodiment, the step of culturing the cell preparation comprising MSC is not part of the method of the present invention.

In one embodiment, culture conditions of the cell preparation comprising MSC are changed before measuring the expression level of at least one growth factor.

As used herein, the term "before measuring the expression level of at least one growth factor" means at least 6 hours, preferably at least 9, 12, 15, 18 or 24 hours between the last passage and the measurement of the expression level of at least one growth factor.

According to one embodiment, the cell preparation comprising MSC is cultured at an oxygen tension of no more than 21%, preferably at most of 15%, more preferably at most of 10% before measuring the expression level of at least one growth factor. In a particular embodiment, the cell preparation comprising MSC is cultured at an oxygen level from about 3% to about 6%, preferably at about 5% $O_2$ corresponding to tissular oxygen tension before measuring the expression level of at least one growth factor. In another embodiment, the cell preparation comprising MSC is cultured at an oxygen level from about 0% to about 1%, at about 0.1% $O_2$ corresponding to hypoxic environment before measuring the expression level of at least one growth factor.

According to another embodiment, the cell preparation comprising MSC is cultured in a medium comprising from about 0.1 to about 10 g/l of glucose, preferably from about 0.5 to about 6 g/l of glucose, more preferably from about 1 to about 4.5 g/l of glucose before measuring the expression level of at least one growth factor.

In one embodiment, the cell preparation comprising MSC is cultured in a medium comprising a low concentration of glucose, corresponding to normal blood sugar levels in vivo, i.e. in a medium comprising from about 0.5 to about 1.5 g/l of glucose, preferably about 1 g/l of glucose before measuring the expression level of at least one growth factor. In another embodiment, the cell preparation comprising MSC is cultured in a medium comprising a high concentration of glucose, corresponding to hyperglycaemic conditions, i.e. in a medium comprising from about 2 to about 10 g/l of glucose, preferably from about 3 to about 6 g/l of glucose, more preferably about 4.5 g/l of glucose before measuring the expression level of at least one growth factor.

In one embodiment, the cell preparation comprising MSC is cultured at about 21% $O_2$ and about 1 g/l glucose before measuring the expression level of at least one growth factor. In another embodiment, the cell preparation comprising MSC is cultured at about 21% $O_2$ and about 4.5 g/l glucose before measuring the expression level of at least one growth factor. In another embodiment, the cell preparation comprising MSC is cultured at about 5% $O_2$ and about 1 g/l glucose before measuring the expression level of at least one growth factor. In another embodiment, the cell preparation comprising MSC is cultured at about 5% $O_2$ and about 4.5 g/l glucose before measuring the expression level of at least one growth factor. In another embodiment, the cell preparation comprising MSC is cultured at about 0.1% $O_2$ and about 1 g/l glucose before measuring the expression level of at least one growth factor. In another embodiment, the cell preparation comprising MSC is cultured at about 0.1% $O_2$ and about 4.5 g/l glucose before measuring the expression level of at least one growth factor.

According to another embodiment, culture conditions of the cell preparation comprising MSC are always the same during all steps of the method of the invention.

In one embodiment of the invention, the method comprises the following steps:
a) culturing a cell preparation comprising mesenchymal stem cells,
b) optionally changing the culture conditions, and
c) quantifying expression level of at least one growth factor, preferably SDF-1α and/or VEGF.

In a preferred embodiment, the method of the invention for assessing the purity of a cell preparation comprising mesenchymal stem cells, preferably adipose stem cells, comprises the following steps:
a) culturing a cell preparation comprising mesenchymal stem cells, preferably adipose stem cells,
b) optionally changing the culture conditions, preferably the $O_2$ tension, and
c) quantifying SDF-la and/or VEGF expression level.

In a particular embodiment, the method of the invention for assessing the purity of a cell preparation comprising mesenchymal stem cells, preferably adipose stem cells, comprises the following steps:
a) culturing a cell preparation comprising mesenchymal stem cells, preferably adipose stem cells,
b) optionally changing the culture conditions, preferably the $0_2$ tension, and
c) quantifying SDF-la expression level.

In a particular embodiment, the method of the invention for assessing the purity of a cell preparation comprising mesenchymal stem cells, preferably adipose stem cells, comprises the following steps:
a) culturing a cell preparation comprising mesenchymal stem cells, preferably adipose stem cells,
b) optionally changing the culture conditions, preferably the $O_2$ tension, and
c) quantifying SDF-la and VEGF expression level.

As used herein, the term "expression" may refer alternatively to the transcription of a growth factor (i.e. expression of the RNA) or to the translation (i.e. expression of the protein) of a growth factor, or to the presence of the growth factor in the supernatant of the cells in culture (i.e. to the secretion of the growth factor).

Methods for determining the expression level are well-known from the skilled artisan, and include, without limitation, determining the transcriptome (in an embodiment wherein expression relates to transcription of a growth factor) or proteome (in an embodiment wherein expression relates to translation or secretion of a growth factor) of a cell.

In one embodiment of the invention, the expression of the growth factor is assessed at the RNA level. Methods for assessing the transcription level of a growth factor are well known in the prior art. Examples of such methods include, but are not limited to, RT-PCR, RT-qPCR, Northern Blot, hybridization techniques such as, for example, use of microarrays, and combination thereof including but not limited to, hybridization of amplicons obtained by RT-PCR, sequencing such as, for example, next-generation DNA sequencing (NGS) or RNA-seq (also known as "Whole Transcriptome Shotgun Sequencing") and the like.

In another embodiment of the invention, the expression of the growth factor is assessed at the protein level. Methods for determining a protein level in a sample are well-known in the art. Examples of such methods include, but are not limited to, immunohistochemistry, Multiplex methods (Luminex), western blot, enzyme-linked immunosorbent assay (ELISA), sandwich ELISA, fluorescent-linked immunosorbent assay (FLISA), enzyme immunoassay (EIA), radioimmunoassay (RIA), flow cytometry (FACS) and the like. Preferably determining the protein level of the growth factor is assessed by enzyme-linked immunosorbent assay (ELISA).

In one embodiment of the invention, determining the expression level of the growth factor specifically corresponds to the detection and quantification of said growth factor secreted in the cell culture supernatant. In a particular embodiment, the method of the invention comprises measuring expression level of SDF-1α and/or VEGF in the cell culture supernatant of the cell preparation comprising MSC.

In one embodiment, the step of measuring the expression level of at least one growth factor is performed when the MSC comprised in the cell preparation are at a density leading to about 80% confluence, preferably to about 85, 90, 95, 99 or 100% confluence.

In the meaning of the invention, the cell preparation comprising MSC is substantially pure when said cell preparation comprises less than 25% of fibroblasts, preferably less than 24, 23, 22, 21, 20, 19, 18, 17, 16, 15, 14, 13, 12 or 11% of fibroblasts. In one embodiment, the cell preparation comprising MSC is substantially pure when said cell preparation comprises less than 10, 9, 8, 7, 6, 5, 4, 3, 2 or 1% of fibroblasts.

According to one embodiment, the cell preparation comprising MSC is substantially pure when the SDF-1α expression level of the cell preparation comprising MSC is at most of 100 pg/ml, preferably at most of 50, 40, 30, 25, 20, 19, 18, 17, 16, 15, 14, 13, 12, 11, 10, 9, 8, 7, 6, 5, 4, 3, 2 or 1 pg/ml.

In one embodiment, the cell preparation comprising MSC is substantially pure when the SDF-1α expression level of the cell preparation comprising MSC cultured at about 21% $O_2$, is at most of 50 pg/ml, preferably at most of 40, 30, 25, 20, 19, 18, 17, 16, 15, 14, 13, 12, 11, 10, 9, 8, 7, 6, 5, 4, 3, 2 or 1 pg/ml.

In another embodiment, the cell preparation comprising MSC is substantially pure when the SDF-1α expression level of the cell preparation comprising MSC cultured at tissular oxygen tension, preferably at about 5% $O_2$, is at most of 50 pg/ml, preferably at most of 40, 30, 25, 20, 19, 18, 17, 16, 15, 14, 13, 12, 11, 10, 9, 8, 7, 6, 5, 4, 3, 2 or 1 pg/ml.

In another embodiment, the cell preparation comprising MSC is substantially pure when the SDF-1α expression level of the cell preparation comprising MSC cultured in hypoxic condition, preferably at about 0.1% $O_2$, is at most of 50 pg/ml, preferably at most of 40, 30, 25, 20, 19, 18, 17, 16, 15, 14, 13, 12, 11, 10, 9, 8, 7, 6, 5, 4, 3, 2 or 1 pg/ml.

In one embodiment, the cell preparation comprising MSC is substantially pure when the SDF-1α expression level of the cell preparation comprising MSC cultured at low concentration of glucose, preferably at about 1 g/l of glucose, is at most of 100 pg/ml, preferably at most of 50, 40, 30, 25, 20, 19, 18, 17, 16, 15, 14, 13, 12, 11, 10, 9, 8, 7, 6, 5, 4, 3, 2 or 1 pg/ml.

In another embodiment, the cell preparation comprising MSC is substantially pure when the SDF-1α expression level of the cell preparation comprising MSC cultured at high concentration of glucose, preferably at about 4.5 g/l of glucose, is at most of 50 pg/ml, preferably at most of 40, 30, 25, 20, 19, 18, 17, 16, 15, 14, 13, 12, 11, 10, 9, 8, 7, 6, 5, 4, 3, 2 or 1 pg/ml.

In one embodiment, the cell preparation comprising MSC is substantially pure when the SDF-1α expression level of the cell preparation comprising MSC cultured at about 21% $O_2$ and at low concentration of glucose, preferably at about 1 g/l of glucose, is at most of 100 pg/ml, preferably at most of 50, 40, 30, 25, 20, 19, 18, 17, 16, 15, 14, 13, 12, 11, 10, 9, 8, 7, 6, 5, 4, 3, 2 or 1 pg/ml.

In another embodiment, the cell preparation comprising MSC is substantially pure when the SDF-1α expression level of the cell preparation comprising MSC cultured at about 21% $O_2$ and at high concentration of glucose, preferably at about 4.5 g/l of glucose, is at most of 50 pg/ml, preferably at most of 40, 30, 25, 20, 19, 18, 17, 16, 15, 14, 13, 12, 11, 10, 9, 8, 7, 6, 5, 4, 3, 2 or 1 pg/ml.

In another embodiment, the cell preparation comprising MSC is substantially pure when the SDF-1α expression level of the cell preparation comprising MSC cultured at tissular oxygen tension, preferably at about 5% $O_2$, and at low concentration of glucose, preferably at about 1 g/l of glucose, is at most of 100 pg/ml, preferably at most of 50, 40, 30, 25, 20, 19, 18, 17, 16, 15, 14, 13, 12, 11, 10, 9, 8, 7, 6, 5, 4, 3, 2 or 1 pg/ml.

In another embodiment, the cell preparation comprising MSC is substantially pure when the SDF-1α expression level of the cell preparation comprising MSC cultured at tissular oxygen tension, preferably at about 5% $O_2$, and at high concentration of glucose, preferably at about 4.5 g/l of glucose, is at most of 50 pg/ml, preferably at most of 40, 30, 25, 20, 19, 18, 17, 16, 15, 14, 13, 12, 11, 10, 9, 8, 7, 6, 5, 4, 3, 2 or 1 pg/ml.

In another embodiment, the cell preparation comprising MSC is substantially pure when the SDF-1α expression level of the cell preparation comprising MSC cultured in hypoxic condition, preferably at about 0.1% $O_2$, and at low concentration of glucose, preferably at about 1 g/l of glucose, is at most of 100 pg/ml, preferably at most of 50, 40, 30, 25, 20, 19, 18, 17, 16, 15, 14, 13, 12, 11, 10, 9, 8, 7, 6, 5, 4, 3, 2 or 1 pg/ml.

In another embodiment, the cell preparation comprising MSC is substantially pure when the SDF-1α expression level of the cell preparation comprising MSC cultured in hypoxic condition, preferably at about 0.1% $O_2$, and at high concentration of glucose, preferably at about 4.5 g/l of glucose, is at most of 50 pg/ml, preferably at most of 40, 30, 25, 20, 19, 18, 17, 16, 15, 14, 13, 12, 11, 10, 9, 8, 7, 6, 5, 4, 3, 2 or 1 pg/ml.

According to one embodiment, the cell preparation comprising MSC is substantially pure when the VEGF expression level of the cell preparation comprising MSC cultured in hypoxic conditions, preferably at about 0.1% $O_2$, and at high concentration of glucose, preferably at about 4.5 g/l of glucose, is at least of 200 pg/ml, preferably at least of 250, 260, 270, 280, 281, 282, 283, 284, 285, 286, 287, 288, 289 or 290 pg/ml.

According to another embodiment, the cell preparation comprising MSC is substantially pure when the VEGF expression level of the cell preparation comprising MSC cultured at tissular oxygen tension, preferably at about 5% $O_2$, and at high concentration of glucose, preferably at about 4.5 g/l of glucose, is at least of 90 pg/ml, preferably at least of 95, 100, 105, 110, 111, 112, 113, 114, 115, 116, 117, 188, 119 or 120 pg/ml.

According to another embodiment, the cell preparation comprising MSC is substantially pure when the VEGF expression level of the cell preparation comprising MSC cultured tissular oxygen tension, preferably at about 5% $O_2$, and at low concentration of glucose, preferably at about 1 g/l of glucose, is at least of 160 pg/ml, preferably at least of 161, 162, 163, 164, 165, 166, 167, 168 or 169 pg/ml, more preferably at least of 170 pg/ml.

In one embodiment, the cell preparation comprising MSC is substantially pure when the cell preparation comprising MSC cultured in hypoxic condition, preferably at about 0.1% $O_2$, and at high concentration of glucose, preferably at about 4.5 g/l of glucose, presents a SDF-1a expression level of at most 50 pg/ml, preferably of at most 40, 30, 25, 20, 19, 18, 17, 16, 15, 14, 13, 12, 11, 10, 9, 8, 7, 6, 5, 4, 3, 2 or 1 pg/ml; and a VEGF expression level of at least 200 pg/ml, preferably of at least 250, 260, 270, 280, 281, 282, 283, 284, 285, 286, 287, 288, 289 or 290 pg/ml.

In another embodiment, the cell preparation comprising MSC is substantially pure when the cell preparation comprising MSC cultured at tissular oxygen tension, preferably at about 5% $O_2$, and at high concentration of glucose, preferably at about 4.5 g/l of glucose, presents a SDF-1a expression level of at most 50 pg/ml, preferably of at most 40, 30, 25, 20, 19, 18, 17, 16, 15, 14, 13, 12, 11, 10, 9, 8, 7, 6, 5, 4, 3, 2 or 1 pg/ml; and a VEGF expression level of at least 90 pg/ml, preferably of at least 95, 100, 105, 110, 111, 112, 113, 114, 115, 116, 117, 188, 119 or 120 pg/ml.

In another embodiment, the cell preparation comprising MSC is substantially pure when the cell preparation comprising MSC cultured at tissular oxygen tension, preferably at about 5% $O_2$, and at low concentration of glucose, preferably at about 1 g/l of glucose, presents a SDF-1α expression level of at most 100 pg/ml, preferably of at most 50, 40, 30, 25, 20, 19, 18, 17, 16, 15, 14, 13, 12, 11, 10, 9, 8, 7, 6, 5, 4, 3, 2 or 1 pg/ml; and a VEGF expression level of at least 160 pg/ml, preferably at least of 161, 162, 163, 164, 165, 166, 167, 168 or 169 pg/ml, more preferably at least of 170 pg/ml.

In one embodiment of the invention, the method comprises the following steps:
a) culturing a cell preparation comprising mesenchymal stem cells,
b) optionally changing the culture conditions, and
c) quantifying secretion of at least one growth factor in the cell culture supernatant, preferably SDF-1α and/or VEGF.

In a preferred embodiment, the method of the invention for assessing the purity of a cell preparation comprising mesenchymal stem cells, preferably adipose stem cells, comprises the following steps:
a) culturing a cell preparation comprising mesenchymal stem cells, preferably adipose stem cells,
b) optionally changing the culture conditions, preferably the $O_2$ tension, and
c) quantifying SDF-1α and/or VEGF secretion in the cell culture supernatant.

In a particular embodiment, the method of the invention for assessing the purity of a cell preparation comprising mesenchymal stem cells, preferably adipose stem cells, comprises the following steps:
a) culturing a cell preparation comprising mesenchymal stem cells, preferably adipose stem cells,
b) optionally changing the culture conditions, preferably the $O_2$ tension, and
c) quantifying SDF-1α secretion in the cell culture supernatant.

In a particular embodiment, the method of the invention for assessing the purity of a cell preparation comprising mesenchymal stem cells, preferably adipose stem cells, comprises the following steps:
a) culturing a cell preparation comprising mesenchymal stem cells, preferably adipose stem cells,
b) optionally changing the culture conditions, preferably the $O_2$ tension, and
c) quantifying SDF-1α and VEGF secretion in the cell culture supernatant.

In one embodiment, the method of the invention further comprises a step of comparing the measured expression level with a reference level.

As used herein, the term "reference" broadly encompasses any suitable reference expression level which may be used as a basis for comparison with respect to the measured expression level.

In one embodiment, the reference is a pure fibroblasts preparation. As used herein, "a pure fibroblasts preparation", e.g. a composition comprising fibroblasts, means a preparation known to be free from any other types of cells than fibroblasts. According to one embodiment, the pure fibroblasts preparation is cultured in the same conditions as the cell preparation comprising MSC.

In one embodiment, the cell preparation comprising MSC is substantially pure when the SDF-1α expression level of the cell preparation comprising MSC is significatively lower than the SDF-1α expression level of the pure fibroblasts preparation. As used herein, the term "significatively lower" means at least 1.5 fold lower, preferably at least 2, 3 or 4 fold lower, more preferably at least 5, 6, 7 or 8 fold lower.

In another embodiment, the cell preparation comprising MSC is substantially pure when the VEGF expression level of the cell preparation comprising MSC is significatively higher than the VEGF expression level of the pure fibroblasts preparation. As used herein, the term "significatively higher" means at least 1.5 fold higher, preferably at least 2 fold higher, more preferably at least 2.1, 2.2, 2.3, 2.4 or 2.5 fold higher.

In another embodiment, the cell preparation comprising MSC is substantially pure when the SDF-1α expression level of the cell preparation comprising MSC is significatively lower than the SDF-1α expression level of the pure fibroblasts preparation and when the VEGF expression level of the cell preparation comprising MSC is significatively higher than the VEGF expression level of the pure fibroblasts preparation.

In another embodiment, the reference sample is a pure mesenchymal stem cells preparation. As used herein, "a pure mesenchymal stem cells preparation", e.g. a composition comprising mesenchymal stem cells, means a preparation known to be free from fibroblasts. According to one embodiment, the pure mesenchymal stem cells preparation is cultured in the same conditions as the cell preparation comprising MSC to be tested.

In one embodiment, the cell preparation comprising MSC is substantially pure when the SDF-1α expression level of the cell preparation comprising MSC is at least 80%, preferably at least 85%, more preferably at least 90%, 95%, 96%, 97%, 98%, 99% or 100% of the SDF-1α expression level of the pure MSC preparation.

In a particular embodiment, the cell preparation comprising MSC is totally pure, i.e. without any fibroblastic contamination, when the SDF-1α expression level of the cell preparation comprising MSC and of the pure MSC preparation are the same.

In another embodiment, the cell preparation comprising MSC is substantially pure when the VEGF expression level of the cell preparation comprising MSC is at least 80%, preferably at least 85%, more preferably at least 90%, 95%, 96%, 97%, 98%, 99% or 100% of the VEGF expression level of the pure cell preparation comprising MSC.

In a particular embodiment, the cell preparation comprising MSC is totally pure, i.e. without any fibroblastic contamination, when the VEGF expression level of the cell preparation comprising MSC and of the pure MSC preparation are the same.

In another embodiment, the cell preparation comprising MSC is substantially pure when the SDF-1α expression level of the cell preparation comprising MSC is at least 80%, preferably at least 85%, more preferably at least 90%, 95%, 96%, 97%, 98%, 99% or 100% of the SDF-1α expression level of the pure MSC preparation and when the VEGF expression level of the cell preparation comprising MSC is at least 80%, preferably at least 85%, more preferably at least 90%, 95%, 96%, 97%, 98%, 99% or 100% of the VEGF expression level of the pure MSC preparation.

In one embodiment of the invention, the method comprises the following steps:
a) culturing a cell preparation comprising mesenchymal stem cells,
b) optionally changing the culture conditions, c) quantifying expression level of at least one growth factor, preferably SDF-1α and/or VEGF, and
d) comparing the expression level measured in step (c) with a reference expression level.

In a preferred embodiment, the method of the invention for assessing the purity of a cell preparation comprising mesenchymal stem cells, preferably adipose stem cells, comprises the following steps:
a) culturing a cell preparation comprising mesenchymal stem cells, preferably adipose stem cells,
b) optionally changing the culture conditions, preferably the $O_2$ tension,
c) quantifying SDF-1α and/or VEGF expression level, and
d) comparing the expression level measured in step (c) with SDF-1α and/or VEGF expression levels of a reference population of cells cultured in the same conditions as MSC.

In a particular embodiment, the method of the invention for assessing the purity of a cell preparation comprising mesenchymal stem cells, preferably adipose stem cells, comprises the following steps:
a) culturing a cell preparation comprising mesenchymal stem cells, preferably adipose stem cells,
b) optionally changing the culture conditions, preferably the $O_2$ tension,
c) quantifying SDF-1α and VEGF expression level, and
d) comparing the expression level measured in step (c) with SDF-1α and VEGF expression levels of a reference population of cells cultured in the same conditions as MSC.

The invention also relates to a cell population identified by the method of the invention as described hereinabove.

In one embodiment, the cell population thus identified is assessed for its purity with respect to fibroblastic contamination.

In one embodiment, the cell population thus identified is substantially pure, i.e. said cell population comprises less than 25% of fibroblasts, preferably less than 24, 23, 22, 21, 20, 19, 18, 17, 16, 15, 14, 13, 12 or 11% of fibroblasts. In one embodiment, the cell preparation thus identified of the invention comprises less than 10, 9, 8, 7, 6, 5, 4, 3, 2 or 1% of fibroblasts.

According to one embodiment, the cell population thus identified presents a SDF-1α expression level of at most 100 pg/ml, preferably at most of 50, 40, 30, 25, 20, 19, 18, 17, 16, 15, 14, 13, 12, 11, 10, 9, 8, 7, 6, 5, 4, 3, 2 or 1 pg/ml.

According to one embodiment, the cell population thus identified presents a SDF-1α expression level of at most 50 pg/ml, preferably at most of 40, 30, 25, 20, 19, 18, 17, 16, 15, 14, 13, 12, 11, 10, 9, 8, 7, 6, 5, 4, 3, 2 or 1 pg/ml when the cell preparation comprising MSC is cultured at about 21% $O_2$.

According to another embodiment, the cell population thus identified presents a SDF-1α expression level of at most 50 pg/ml, preferably at most of 40, 30, 25, 20, 19, 18, 17, 16, 15, 14, 13, 12, 11, 10, 9, 8, 7, 6, 5, 4, 3, 2 or 1 pg/ml when the cell preparation comprising MSC is cultured at tissular oxygen tension, preferably at about 5% $O_2$.

According to another embodiment, the cell population thus identified presents a SDF-1α expression level of at most 50 pg/ml, preferably at most of 40, 30, 25, 20, 19, 18, 17, 16, 15, 14, 13, 12, 11, 10, 9, 8, 7, 6, 5, 4, 3, 2 or 1 pg/ml when the cell preparation comprising MSC is cultured in hypoxic conditions, preferably at about 0.1% $O_2$.

According to one embodiment, the cell population thus identified presents a SDF-1α expression level of at most 100 pg/ml, preferably at most of 50, 40, 30, 25, 20, 19, 18, 17, 16, 15, 14, 13, 12, 11, 10, 9, 8, 7, 6, 5, 4, 3, 2 or 1 pg/ml when the cell preparation comprising MSC is cultured at low concentration of glucose, preferably at about 1 g/l of glucose.

According to another embodiment, the cell population thus identified presents a SDF-1α expression level of at most 50 pg/ml, preferably at most of 40, 30, 25, 20, 19, 18, 17, 16, 15, 14, 13, 12, 11, 10, 9, 8, 7, 6, 5, 4, 3, 2 or 1 10 pg/ml when the cell preparation comprising MSC is cultured at high concentration of glucose, preferably at about 4.5 g/l of glucose.

In one embodiment, the cell population thus identified presents a SDF-1α expression level of at most 100 pg/ml, preferably at most of 50, 40, 30, 25, 20, 19, 18, 17, 16, 15, 14, 13, 12, 11, 10, 9, 8, 7, 6, 5, 4, 3, 2 or 1 pg/ml when the cell preparation comprising MSC is cultured at about 21% $O_2$ and at low concentration of glucose, preferably at about 1 g/l of glucose.

In another embodiment, the cell population thus identified presents a SDF-1α expression level of at most 50 pg/ml, preferably at most of 40, 30, 25, 20, 19, 18, 17, 16, 15, 14, 13, 12, 11, 10, 9, 8, 7, 6, 5, 4, 3, 2 or 1 pg/ml when the cell preparation comprising MSC is cultured at about 21% $O_2$ and at high concentration of glucose, preferably at about 4.5 g/l of glucose.

In one embodiment, the cell population thus identified presents a SDF-1α expression level of at most 100 pg/ml, preferably at most of 50, 40, 30, 25, 20, 19, 18, 17, 16, 15, 14, 13, 12, 11, 10, 9, 8, 7, 6, 5, 4, 3, 2 or 1 pg/ml when the cell preparation comprising MSC is cultured at tissular oxygen tension, preferably at about 5% $O_2$, and at low concentration of glucose, preferably at about 1 g/l of glucose.

In another embodiment, the cell population thus identified presents a SDF-1α expression level of at most 50 pg/ml, preferably at most of 40, 30, 25, 20, 19, 18, 17, 16, 15, 14, 13, 12, 11, 10, 9, 8, 7, 6, 5, 4, 3, 2 or 1 pg/ml when the cell preparation comprising MSC is cultured at tissular oxygen tension, preferably at about 5% $O_2$, and at high concentration of glucose, preferably at about 4.5 g/l of glucose.

In one embodiment, the cell population thus identified presents a SDF-1α expression level of at most 100 pg/ml, preferably at most of 50, 40, 30, 25, 20, 19, 18, 17, 16, 15, 14, 13, 12, 11, 10, 9, 8, 7, 6, 5, 4, 3, 2 or 1 pg/ml when the cell preparation comprising MSC is cultured in hypoxic conditions, preferably at about 0.1% $O_2$, and at low concentration of glucose, preferably at about 1 g/l of glucose.

In another embodiment, the cell population thus identified presents a SDF-1α expression level of at most 50 pg/ml, preferably at most of 40, 30, 25, 20, 19, 18, 17, 16, 15, 14, 13, 12, 11, 10, 9, 8, 7, 6, 5, 4, 3, 2 or 1 pg/ml when the cell preparation comprising MSC is cultured in hypoxic conditions, preferably at about 0.1% $O_2$, and at high concentration of glucose, preferably at about 4.5 g/l of glucose.

According to one embodiment, the cell population thus identified presents a VEGF expression level of at least of 200 pg/ml, preferably at least of 250, 260, 270, 280, 281, 282, 283, 284, 285, 286, 287, 288, 289 or 290 pg/ml when the cell preparation comprising MSC is cultured in hypoxic conditions, preferably at about 0.1% $O_2$, and high concentration of glucose, preferably at about 4.5 g/l of glucose.

According to another embodiment, the cell population thus identified presents a VEGF expression level of at least of 90 pg/ml, preferably at least of 95, 100, 105, 110, 111, 112, 113, 114, 115, 116, 117, 118, 119 or 120 pg/ml when the cell preparation comprising MSC is cultured at tissular oxygen tension, preferably at about 5% $O_2$, and high concentration of glucose, preferably at about 4.5 g/l of glucose.

According to another embodiment, the cell population thus identified presents a VEGF expression level of at least of 160 pg/ml, preferably at least of 161, 162, 163, 164, 165, 166, 167, 168 or 169 pg/ml, more preferably at least of 170 pg/ml when the cell preparation comprising MSC is cultured at tissular oxygen tension, preferably at about 5% $O_2$, and low concentration of glucose, preferably at about 1 g/l of glucose.

In one embodiment, the cell population thus identified presents a SDF-1α expression level of at most 50 pg/ml, preferably of at most 40, 30, 25, 20, 19, 18, 17, 16, 15, 14, 13, 12, 11, 10, 9, 8, 7, 6, 5, 4, 3, 2 or 1 pg/ml; and a VEGF expression level of at least 200 pg/ml, preferably of at least 250, 206, 270, 280, 281, 282, 283, 284, 285, 286, 287, 288, 289 or 290 pg/ml, when the cell preparation comprising MSC is cultured in hypoxic conditions, preferably at about 0.1% $O_2$, and at high concentration of glucose, preferably at about 4.5 g/l of glucose.

In another embodiment, the cell population thus identified presents a SDF-1α expression level of at most 50 pg/ml, preferably of at most 40, 30, 25, 20, 19, 18, 17, 16, 15, 14, 13, 12, 11, 10, 9, 8, 7, 6, 5, 4, 3, 2 or 1 pg/ml; and a VEGF expression level of at least 90 pg/ml, preferably of at least 95, 100, 105, 110, 111, 112, 113, 114, 115, 116, 117, 118, 119 or 120 pg/ml, when the cell preparation comprising MSC is cultured at 5% $O_2$ and high concentration of glucose, preferably at about 4.5 g/l of glucose.

In another embodiment, the cell preparation thus identified presents a SDF-1α expression level of at most 100 pg/ml, preferably of at most 50, 40, 30, 25, 20, 19, 18, 17, 16, 15, 14, 13, 12, 11, 10, 9, 8, 7, 6, 5, 4, 3, 2 or 1 pg/ml; and a VEGF expression level of at least 160 pg/ml, preferably at least of 161, 162, 163, 164, 165, 166, 167, 168 or 169 pg/ml, more preferably at least of 170 pg/ml, when the cell preparation comprising MSC is cultured at 5% $O_2$ and low concentration of glucose, preferably at about 1 g/l of glucose.

Another object of the invention is a substantially pure mesenchymal stem cells population, preferably an adipose stem cells population.

In one embodiment, the substantially pure cell population of the invention comprises less than 25% of fibroblasts, preferably less than 24, 23, 22, 21, 20, 19, 18, 17, 16, 15, 14, 13, 12 or 11% of fibroblasts. In one embodiment, the cell preparation of the invention comprises less than 10, 9, 8, 7, 6, 5, 4, 3, 2 or 1% of fibroblasts.

According to one embodiment, the substantially pure cell population of the invention presents a SDF-1α expression level of at most 100 pg/ml, preferably at most of 50, 40, 30, 25, 20, 19, 18, 17, 16, 15, 14, 13, 12, 11, 10, 9, 8, 7, 6, 5, 4, 3, 2 or 1 pg/ml.

According to one embodiment, the substantially pure cell population of the invention presents a SDF-1α expression level of at most 50 pg/ml, preferably at most of 40, 30, 25, 20, 19, 18, 17, 16, 15, 14, 13, 12, 11, 10, 9, 8, 7, 6, 5, 4, 3, 2 or 1 pg/ml when cultured at about 21% $O_2$.

According to another embodiment, the substantially pure cell population of the invention presents a SDF-1α expression level of at most 50 pg/ml, preferably at most of 40, 30, 25, 20, 19, 18, 17, 16, 15, 14, 13, 12, 11, 10, 9, 8, 7, 6, 5, 4, 3, 2 or 1 pg/ml when cultured at tissular oxygen tension, preferably at about 5% $O_2$.

According to another embodiment, the substantially pure cell population of the invention presents a SDF-1α expression level of at most 50 pg/ml, preferably at most of 40, 30, 25, 20, 19, 18, 17, 16, 15, 14, 13, 12, 11, 10, 9, 8, 7, 6, 5, 4, 3, 2 or 1 pg/ml when cultured in hypoxic conditions, preferably at about 0.1% $O_2$.

According to one embodiment, the substantially pure cell population of the invention presents a SDF-1α expression level of at most 100 pg/ml, preferably at most of 50, 40, 30, 25, 20, 19, 18, 17, 16, 15, 14, 13, 12, 11, 10, 9, 8, 7, 6, 5, 4, 3, 2 or 1 pg/ml when cultured at low concentration of glucose, preferably at about 1 g/l of glucose.

According to another embodiment, the substantially pure cell population of the invention presents a SDF-1α expression level of at most 50 pg/ml, preferably at most of 40, 30, 25, 20, 19, 18, 17, 16, 15, 14, 13, 12, 11, 10, 9, 8, 7, 6, 5, 4, 3, 2 or 1 pg/ml when cultured at high concentration of glucose, preferably at about 4.5 g/l of glucose.

In one embodiment, the substantially pure cell population of the invention presents a SDF-1α expression level of at most 100 pg/ml, preferably at most of 50, 40, 30, 25, 20, 19, 18, 17, 16, 15, 14, 13, 12, 11, 10, 9, 8, 7, 6, 5, 4, 3, 2 or 1 pg/ml when cultured at about 21% $O_2$ and at low concentration of glucose, preferably at about 1 g/l of glucose.

In another embodiment, the substantially pure cell population of the invention presents a SDF-1α expression level of at most 50 pg/ml, preferably at most of 40, 30, 25, 20, 19, 18, 17, 16, 15, 14, 13, 12, 11, 10, 9, 8, 7, 6, 5, 4, 3, 2 or 1 pg/ml when cultured at about 21% $O_2$ and at high concentration of glucose, preferably at about 4.5 g/l of glucose.

In one embodiment, the substantially pure cell population of the invention presents a SDF-1α expression level of at most 100 pg/ml, preferably at most of 50, 40, 30, 25, 20, 19, 18, 17, 16, 15, 14, 13, 12, 11, 10, 9, 8, 7, 6, 5, 4, 3, 2 or 1 pg/ml when cultured at tissular oxygen tension, preferably at about 5% $O_2$, and at low concentration of glucose, preferably at about 1 g/l of glucose.

In another embodiment, the substantially pure cell population of the invention presents a SDF-1α expression level of at most 50 pg/ml, preferably at most of 40, 30, 25, 20, 19, 18, 17, 16, 15, 14, 13, 12, 11, 10, 9, 8, 7, 6, 5, 4, 3, 2 or 1 pg/ml when cultured at tissular oxygen tension, preferably at about 5% $O_2$, and at high concentration of glucose, preferably at about 4.5 g/l of glucose.

In one embodiment, the substantially pure cell population of the invention presents a SDF-1α expression level of at most 100 pg/ml, preferably at most of 50, 40, 30, 25, 20, 19, 18, 17, 16, 15, 14, 13, 12, 11, 10, 9, 8, 7, 6, 5, 4, 3, 2 or 1 pg/ml when cultured in hypoxic conditions, preferably at about 0.1% $O_2$, and at low concentration of glucose, preferably at about 1 g/l of glucose.

In another embodiment, the substantially pure cell population of the invention presents a SDF-1α expression level of at most 50 pg/ml, preferably at most of 40, 30, 25, 20, 19, 18, 17, 16, 15, 14, 13, 12, 11, 10, 9, 8, 7, 6, 5, 4, 3, 2 or 1 pg/ml when cultured in hypoxic conditions, preferably at about 0.1% $O_2$, and at high concentration of glucose, preferably at about 4.5 g/l of glucose.

According to one embodiment, the substantially pure cell population of the invention presents a VEGF expression level of at least of 200 pg/ml, preferably at least of 250, 260, 270, 280, 281, 282, 283, 284, 285, 286, 287, 288, 289 or 290 pg/ml when cultured in hypoxic conditions, preferably at about 0.1% $O_2$, and high concentration of glucose, preferably at about 4.5 g/l of glucose.

According to another embodiment, the substantially pure cell population of the invention presents a VEGF expression level of at least of 90 pg/ml, preferably at least of 95, 100, 105, 110, 111, 112, 113, 114, 115, 116, 117, 118, 119 or 120 pg/ml when cultured at tissular oxygen tension, preferably at about 5% $O_2$, and high concentration of glucose, preferably at about 4.5 g/l of glucose.

According to another embodiment, the substantially pure cell population of the invention presents a VEGF expression level of at least of 160 pg/ml, preferably at least of 161, 162, 163, 164, 165, 166, 167, 168 or 169 pg/ml, more preferably at least of 170 pg/ml when cultured at tissular oxygen tension, preferably at about 5% $O_2$, and low concentration of glucose, preferably at about 1 g/l of glucose.

In one embodiment, the substantially pure cell population of the invention presents a SDF-1α expression level of at most 50 pg/ml, preferably of at most 40, 30, 25, 20, 19, 18, 17, 16, 15, 14, 13, 12, 11, 10, 9, 8, 7, 6, 5, 4, 3, 2 or 1 pg/ml; and a VEGF expression level of at least 200 pg/ml, preferably of at least 250, 206, 270, 280, 281, 282, 283, 284, 285, 286, 287, 288, 289 or 290 pg/ml, when cultured in hypoxic conditions, preferably at about 0.1% $O_2$, and high concentration of glucose, preferably at about 4.5 g/l of glucose.

In another embodiment, the substantially pure cell population of the invention presents a SDF-1α expression level of at most 50 pg/ml, preferably of at most 40, 30, 25, 20, 19, 18, 17, 16, 15, 14, 13, 12, 11, 10, 9, 8, 7, 6, 5, 4, 3, 2 or 1 pg/ml; and a VEGF expression level of at least 90 pg/ml, preferably of at least 95, 100, 105, 110, 111, 112, 113, 114, 115, 116, 117, 118, 119 or 120 pg/ml, when cultured at tissular oxygen tension, preferably at about 5% $O_2$, and high concentration of glucose, preferably at about 4.5 g/l of glucose.

In another embodiment, the substantially pure cell population of the invention presents a SDF-1α expression level of at most 100 pg/ml, preferably of at most 50, 40, 30, 25, 20, 19, 18, 17, 16, 15, 14, 13, 12, 11, 10, 9, 8, 7, 6, 5, 4, 3, 2 or 1 pg/ml; and a VEGF expression level of at least 160 pg/ml, preferably at least of 161, 162, 163, 164, 165, 166, 167, 168 or 169 pg/ml, more preferably at least of 170 pg/ml, when cultured at tissular oxygen tension, preferably at about 5% $O_2$, and low concentration of glucose, preferably at about 1 g/l of glucose.

Another object of the invention is a kit for implementing the method of the invention, wherein said kit comprises means for determining or measuring the expression level of at least one growth factor of a mesenchymal stem cells (MSC) preparation, preferably SDF-1α and/or VEGF.

In one embodiment, the expression level of at least one growth factor is assessed at the protein level, and the kit of the invention may comprise means for detecting the at least one growth factor, preferably SDF-1α and/or VEGF. In one embodiment, said means for detecting the at least one growth factor is an antibody specific of said at least one growth factor, preferably SDF-1α and/or VEGF. In one embodiment, the kit of the invention may also comprise means for detecting the expression level of at least one normalization protein.

In another embodiment, the expression level of at least one growth factor is assessed at the RNA level, and the kit of the invention may comprise means for total RNA extraction, means for reverse transcription of total RNA, and means for quantifying the expression of RNA of at least one growth factor, preferably VEGF and/or SDF-1α. In one embodiment, the means for quantifying the expression of RNA of at least one growth factor, preferably SDF-1α and/or VEGF are PCR or qPCR primers specific for said growth factor, preferably SDF-1α and/or VEGF. In one embodiment, the kit also comprises reagents for carrying out a quantitative PCR (such as, for example, buffers, enzyme, and the like). In one embodiment, the kit of the invention may also comprise means for detecting the expression level of at least one normalization gene at the RNA level.

According to one embodiment, the kit of the invention further comprises the reference for comparing the measured expression level of the at least one growth factor.

In one embodiment, the kit of the invention further comprises a pure fibroblasts preparation. In another embodiment, the kit of the invention further comprises a pure MSC preparation.

In one embodiment, the kit of the invention comprises the supernatant of a pure fibroblasts preparation. In another embodiment, the kit of the invention comprises the supernatant of a pure MSC preparation. In another embodiment, the kit of the invention comprises a range of dilution of pure MSC preparation supernatant and pure fibroblasts preparation supernatant. An example of dilution range is, without limitation, 100/0, 75/25, 50/50, 25/75, 0/100.

The present invention also relates to a growth factor, preferably SDF-1α and/or VEGF, as a biomarker of the quality or purity of a cell preparation comprising MSC, in particular of a cell preparation comprising MSC to be used as MSC-based cell therapy product in regenerative medicine.

In a particular embodiment, the invention concerns a growth factor, preferably SDF-1α and/or VEGF, as a biomarker of the quality or purity of an ASC preparation.

BRIEF DESCRIPTION OF THE DRAWINGS

FIG. 3 is a histogram showing the cell survival of ASC and DF in proliferation medium without FBS, at 0.1 or 5% $O_2$.

EXAMPLES

Figure 1:
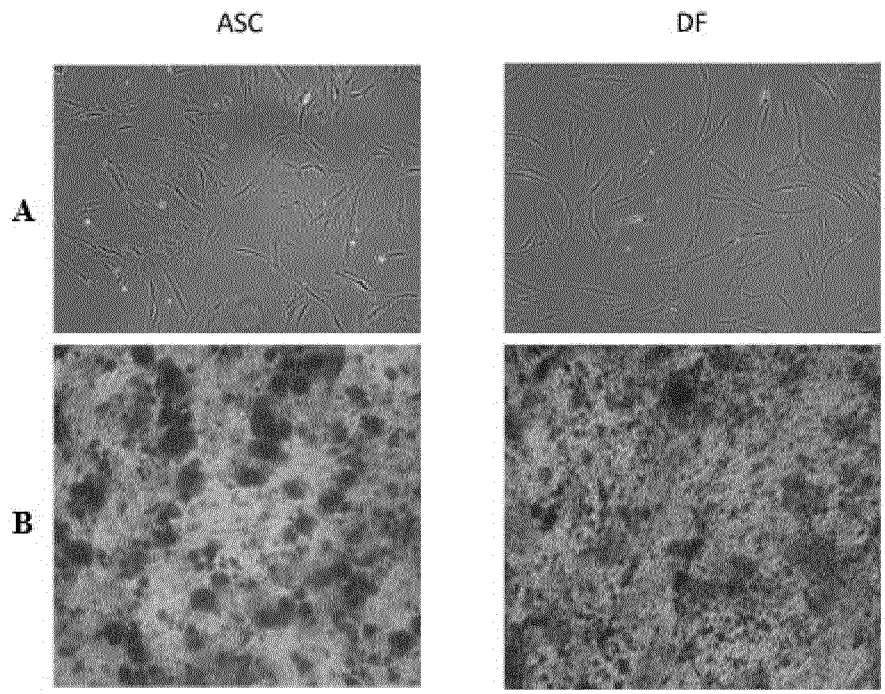
FIG. 1 is a photograph showing ASC and DF in proliferation medium (A) and in osteogenic differentiation medium (B).

The present invention is further illustrated by the following examples.

Example 1

Materials and Methods
This study was performed according to the guidelines of the Belgian Ministry of Health. All procedures were approved by the Ethical Committee of the Medical Faculty (Université Catholique de Louvain) for tissue procurement and clinical study (B40320108280). All materials were obtained from Lonza (Verviers, Switzerland), Sigma-Aldrich (St. Louis, Mo., USA), or Invitrogen (Carlsbad, Calif., USA) unless otherwise noted.

ASC and DF Isolation and Culture

A combined harvesting of human adipose (mean: 7.4 g) and dermal (mean: 1.5 $cm^2$) tissues were performed in 8 patients (Table 1) undergoing elective plastic surgery after informed consent and serologic screening, by lipoaspiration using the Coleman technique, and skin biopsy, respectively. Adipose tissue and skin samples were kept in sterile conditions for a maximum of 60 minutes at 4° C. before adipose-derived stem cells (ASC) and dermal fibroblasts (DF) isolation.

anti-CD105, anti-CD146, anti-CD166, anti-CD44, anti-CD19, anti-CD45 (Human Mesenchymal Stem Cell marker antibody panel, R&D System, Minneapolis, Minn., USA), anti-CD44 (PE mouse anti-human CD44, BD Bioscience, Franklin Lakes, N.J., USA), anti-CD73 (FITC mouse anti-human CD73, BD Bioscience), anti-CD31 (FITC, mouse anti-human, Abcam, Cambridge, UK), anti-CD11b (FITC, mouse anti-human, Abcam, Cambridge, UK), anti-CD79a (PE, mouse anti-human, Abcam, Cambridge, UK), anti-CD13 (FITC, mouse anti-human, Abcam, Cambridge, UK), anti-HLA-DR (FITC, mouse anti-human, Abcam, Cambridge, UK), anti-CD14 (FITC, mouse anti-human, Abcam, Cambridge, UK), anti-CD34 (PE, mouse anti-human, Abcam, Cambridge, UK). At least 10,000 gated events were analyzed by flow cytometry with CellquestPro software. Results are expressed in mean fluorescence intensity (MFI), and expressed as percentage of positive cells (threshold: 95% of isotype).

TABLE 1

Coupled ASC/DF donors characteristics

| Donor | 1 | 2 | 3 | 4 | 5 | 6 | 7 | 8 |
|---|---|---|---|---|---|---|---|---|
| Age (years) | 19 | 44 | 40 | 62 | 56 | 46 | 45 | 41 |
| Sex | F | F | F | F | F | F | F | F |
| Clinical indication | mammaplasty | abdominoplasty | mammaplasty | Lat. Dorsi flap | abdominoplasty | mammaplasty | mammaplasty | mammaplasty |

The adipose tissue was digested with collagenase (1/2 w/v) in a water bath at 37° C. for 60 minutes. Collagenase was inactivated in Dulbecco's modified Eagle medium (DMEM) supplemented with 10% fetal bovine serum. Collected tissue was centrifuged for 10 minutes at 1500 rpm at room temperature. The pellet was suspended in a proliferation medium made up of DMEM supplemented with 10% fetal bovine serum, L-glutamine (2 mM), and antibiotics (100 U/ml penicillin, 100 µg/ml streptomycin, and 1 µl/ml amphotericin B) and filtered through a 500-µm mesh screen. The collected suspension was then seeded in 25 $cm^2$ culture flasks with proliferation medium.

DF were isolated by extraction from de-epidermized dermal biopsies, minced in 2 mm×2 mm fragments and placed in plastic well. Small volume of the proliferation medium was added to avoid detachment from the plastic surface.

After 24 hours of incubation at 37° C. and 5% $CO_2$, the proliferation media were replaced. This initial passage of the primary cells is referred to as passage 0. Dermal pieces were removed from the culture dish when adherent cells were visible on the plastic surface surrounding tissue fragments. Cells were maintained in proliferation medium (changed 2 times/week) up to passage 4, after sequential trypsinizations. Cells from 3 donors were cultivated until passage 15 to study the proliferation profile in standard culture conditions (37° C., 21% $O_2$, 5% $CO_2$, 4.5 g/l glucose).

Membrane Marker Profile Characterization

At passage 4, ASC and DF were characterized for standard cell surface markers (CD44, CD45, CD73, CD90, CD105, stro-1, CD106, CD146, CD166, CD19, CD31, CD11b, CD79α, CD13, HLA-DR, CD14, CD34) [Dominici et al., Cytotherapy. 2006; 8(4):315-317; Bourin et al., Cytotherapy. 2013; 15:641-648] by fluorescence-activated cell sorting (FACScan; BD Biosciences, San Jose, Calif.).

Briefly, ASC were stained with saturating amounts of monoclonal antibodies: anti-Stro-1, anti-CD90, anti-CD106, Differentiation Capacity ASC and DF were tested at passage 4 in specific media to assess the capacity of differentiation toward osteogenic lineage. The differentiation was evaluated by Alizarin red staining after culturing the cell during 3 weeks in specific differentiation medium (proliferation medium supplemented with dexamethasone (1 µM), sodium ascorbate (50 µg/ml), and sodium dihydrophosphate (36 mg/ml) [Qu et al., In Vitro Cell Dev Biol Anim. 2007; 43:95-100]. Osteogenic differentiation was confirmed by staining for calcium phosphate with Alizarin red after formalin fixation. In addition, immunohistochemistry for osteocalcin was performed to confirm the bone phenotype.

Impact of Oxygen Tension and Fetal Bovine Serum (FBS) on Cell Proliferation: EdU Assay Cell proliferation capacity was tested by direct DNA synthesis measurement by 5-ethynyl-2'-deoxyuridine incorporation using Click-iT® EdU Alexa Fluor® 488 Flow Cytometry Assay Kit (Life Technology, Waltham, Mass., USA). ASC (n=3) and DF (n=3) were seeded in 21.5 $cm^2$ culture dishes at a density of 5000 cells/$cm^2$, and cultured for 24 hours in 10% FBS, 21% $O_2$. Cells proliferation was then stopped by replacing the proliferation medium by the same, without FBS, for 24 hours. The cells were finally placed for 48 hours in the specific conditions: 0.1% $O_2$, 5% $O_2$ and 21% $O_2$ in proliferation medium supplemented with 1% FBS or 5% FBS and EdU (5-ethynyl-2'-deoxyuridine, a nucleoside analog of thymidine and incorporated into DNA during active DNA synthesis) was added. After revelation with Alexa Fluor® 488, positive cells were counted by flow cytometry (FACScan; BD Biosciences, San Jose, Calif.).

Growth Factor Secretion Profile

After trypsinization, cells (after passage 3) were counted and 5 progressive dilutions were obtained: 100% ASC+0% DF; 75% ASC+25% DF; 50% ASC+50% DF; 25% ASC+75% DF; and 0% ASC+100% DF, and seeded in 12-well culture plates with cells at a density leading to about 80% to 95% confluence in triplicate for incubation in hypoxic chambers (Modular Incubator Chamber MIC-101; Billups-Rothenberg, Del Mar, Calif., USA) at 0.1% $O_2$ and 5% $O_2$, corresponding to highly hypoxic environment and tissular oxygen tension, respectively. The cells were exposed (for each dilution and oxygen tension) to normoglycaemic (1 g/L) or hyperglycaemic (4.5 g/L) proliferation media. After incubation for 24 hours in these controlled conditions; cell culture supernatants were harvested individually and stored at −20° C. for further growth factor quantification by enzyme-linked immunosorbent assay (VEGF, HGF, IGF-1, SDF-1α and basic FGF by Quantikine ELISA kit; R&D System, Minneapolis, Minn., USA). Cellular viability was assessed immediately after the hypoxic stress by 3-(4,5-dimethylthiazol-2-yl)-5-(3-carboxymethoxyphenyl)-2-(4-sulfophenyl)-2H-tetrazolium solution (MTS; Promega, Leiden, the Netherlands) assay. Hypoxic/glycaemic stress tests and growth factor quantifications were performed in triplicate and duplicate, respectively. Results are expressed in picograms per millimeter.

Statistical Analysis

The one-sample Kolmogorov test and Q-Q plots were used to assess the normal distribution of values. Statistically significant differences between groups (with normal distribution) were tested by paired t-test and one-way analysis of variance with the Bonferroni post hoc test. Statistical tests were performed with PASW 18 (SPSS; IBM, New York, N.Y., USA); $p<0.05$ was considered significant.

Results

Surface marker profiles do not allow the distinction between the two cell populations (Table 2).

TABLE 2

Surface marker characterization of human ASC and DF

|  | ASC % of positive cells | DF % of positive cells |
|---|---|---|
| Mesenchymal (stromal) cells markers | | |
| CD13 | 99.06 | 99.86 |
| CD44 | 95.53 | 99.97 |
| CD73 | 93.78 | 99.86 |
| CD90 | 98.63 | 100.00 |
| CD105 | 96.86 | 99.78 |
| CD166 | 60.74 | 96.51 |
| Bone marrow-derived MSC markers | | |
| CD106 | 5.41 | 2.83 |
| Stro-1 | 4.03 | 5.73 |
| CD146 | 7.16 | 33.91 |
| Endothelial cells markers | | |
| CD31 | 5.59 | 5.41 |
| Hematopoietic lineage markers | | |
| CD14 | 6.75 | 28.27 |
| CD45 | 5.15 | 0.62 |
| CD11b | 5.80 | 8.65 |
| CD34 | 5.53 | 0.54 |
| Human leukocyte antigens | | |
| HLA-DR | 6.52 | 1.65 |
| CD19 | 4.51 | 2.05 |
| CD79α | 5.10 | 0.37 |

ASC and DF were positive (>90% of positive cells) for mesenchymal cell markers (CD13, CD44, CD73, CD90, CD105, CD166), negative for endothelial (CD31), bone-marrow-derived stromal cells (CD106, Stro-1, CD146) and hematopoietic markers (CD14, CD45, CD11b, CD34), and for HLA-DR, CD79α and CD19. After culture in specific differentiation media (FIG. 1), osteogenic differentiation capacity was demonstrated for both ASC and DF by Alizarin red staining and osteocalcin immunohistochemistry.

Figure 2:
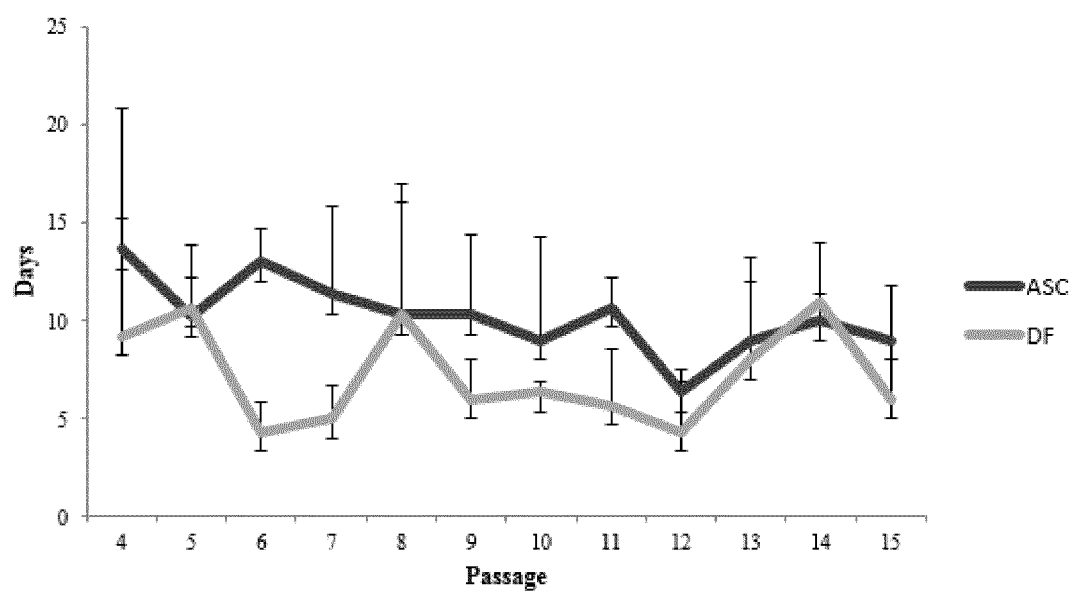
FIG. 2 is a graph showing the cell proliferation of ASC and DF according to the number of passages.

ASC and DF had similar proliferation profile until passage 15 (FIG. 2, NS).

ASC and DF viability was not significantly impacted after 24 hours of culture at 0.1% $O_2$ and 5% $O_2$ without FBS (FIG. 3). At 5% $O_2$, DF viability was reduced when compared to ASC (87.04% of ASC survival, $p<0.05$).

Figure 4:
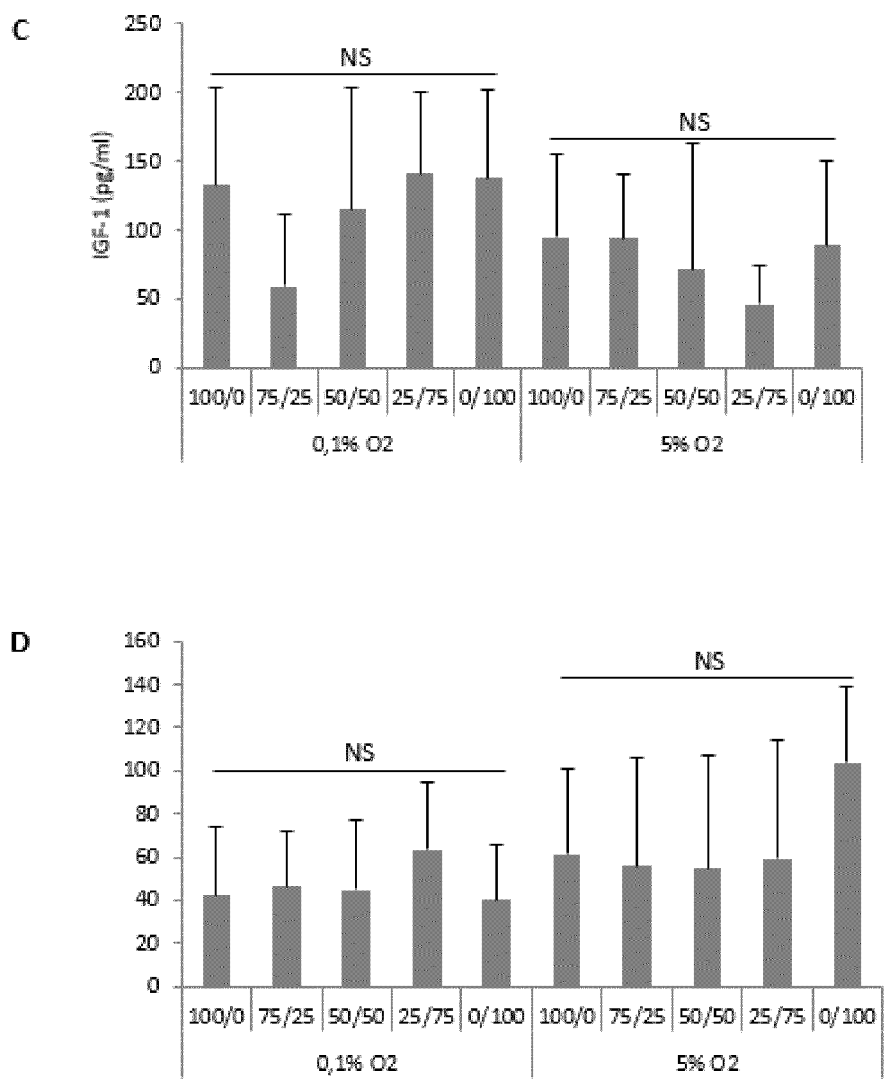
FIG. 4 is a set of histograms showing KGF secretion (A), b-FGF secretion (B), IGF-1 secretion (C), and HGF secretion (D) of 5 different ASC/DF dilutions in proliferation medium with 4.5 g/l glucose, at 0.1 or 5% $O_2$.

The study of HGF, IGF-1, bFGF and KGF secretion (at 0.1% and 5% $O_2$, 4.5 g/l glucose) from the sequential dilutions of ASC and DF did not demonstrate any significant curve (FIG. 4).

Figure 5:
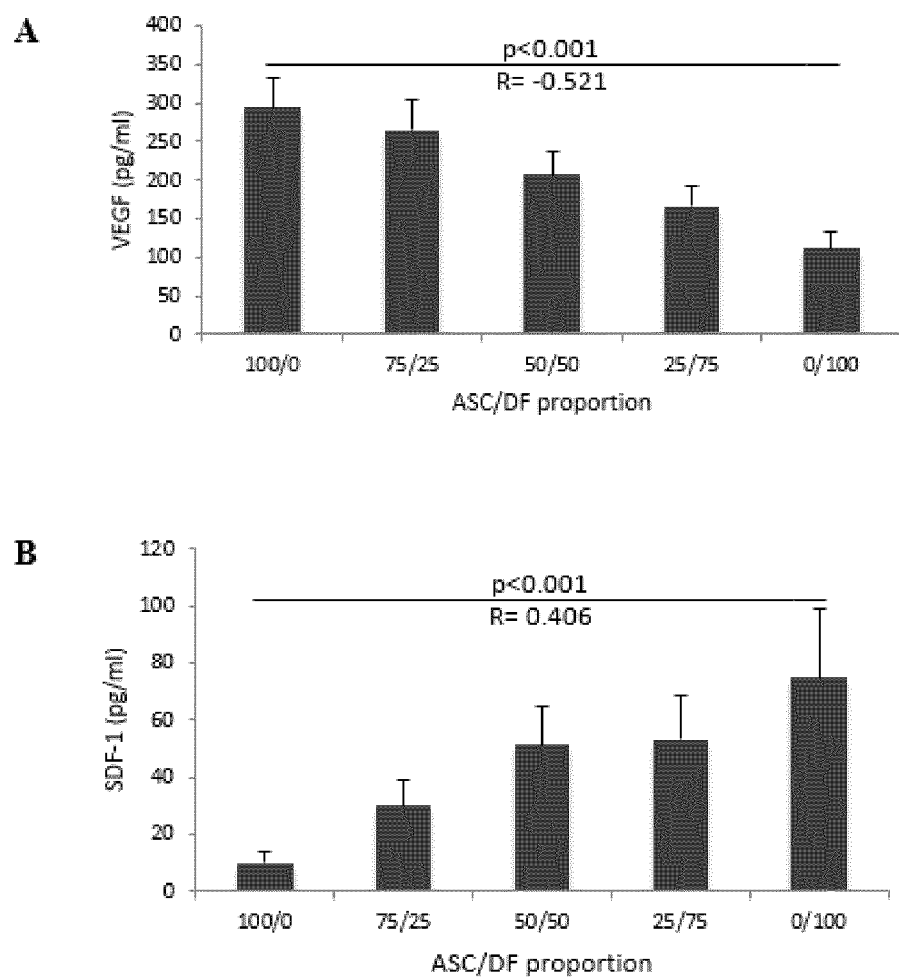
FIG. 5 is a set of histograms showing VEGF secretion (A) and SDF-1α secretion (B) of 5 different ASC/DF dilutions in proliferation medium with 4.5 g/l glucose, at 0.1% $O_2$.
Figure 6:
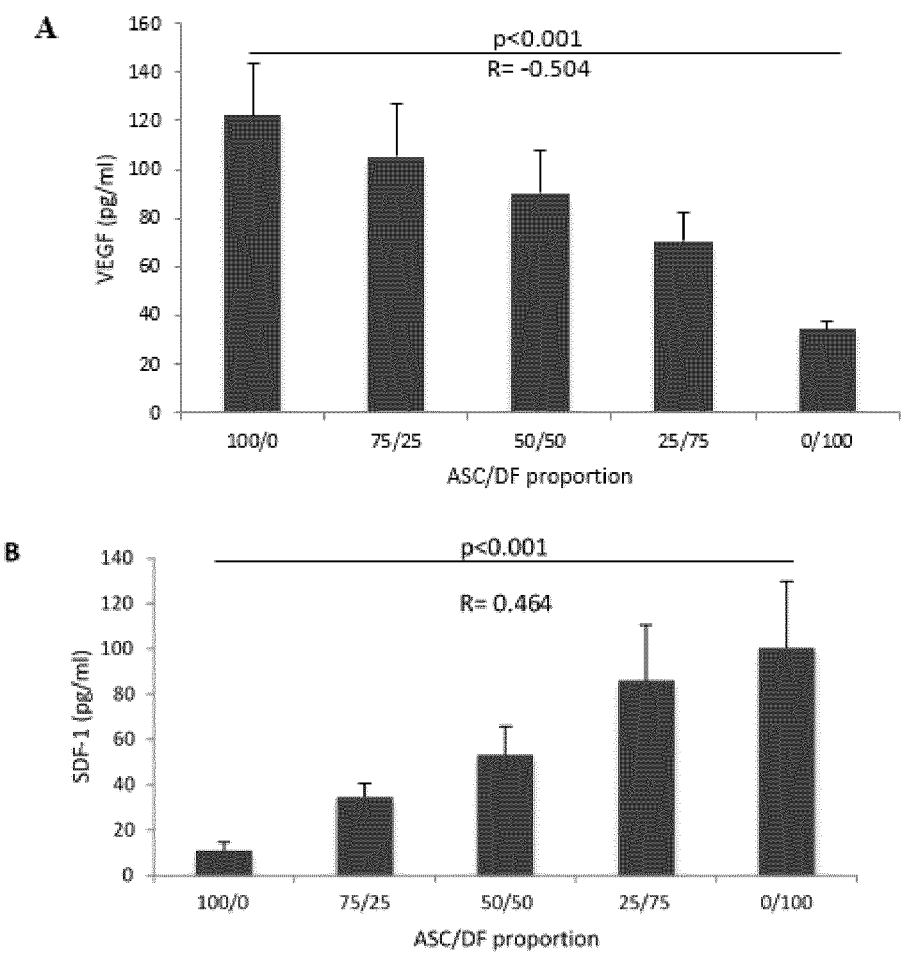
FIG. 6 is a set of histograms showing VEGF secretion (A) and SDF-1α secretion (B) of 5 different ASC/DF dilutions in proliferation medium with 4.5 g/l glucose, at 5% $O_2$.
Figure 7:
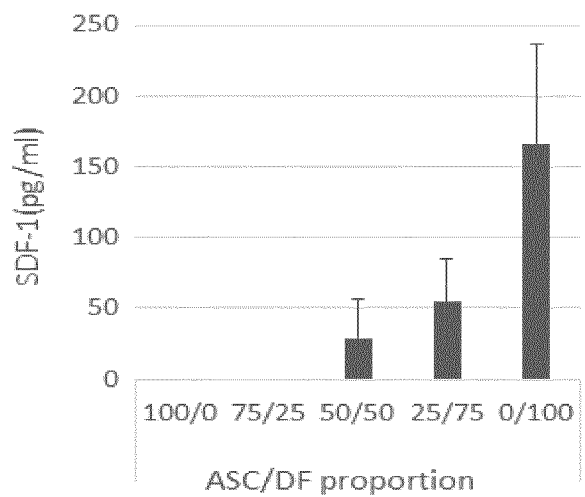
FIG. 7 is a histogram showing SDF-1α secretion of 5 different ASC/DF dilutions in proliferation medium with 4.5 g/l glucose, at 21% $O_2$.
Figure 8:
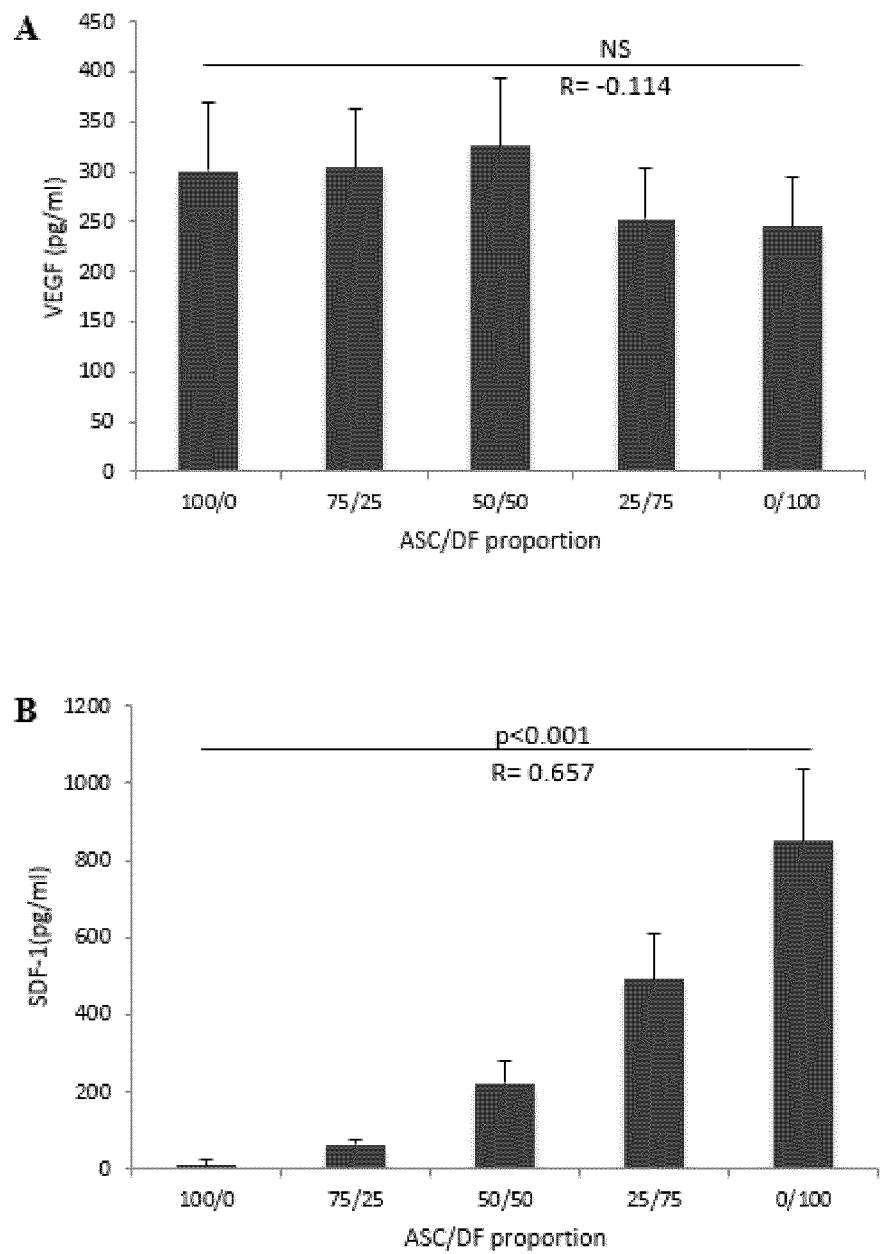
FIG. 8 is a set of histograms showing VEGF secretion (A) and SDF-1α secretion (B) of 5 different ASC/DF dilutions in proliferation medium with 1 g/l glucose, at 0.1% $O_2$.
Figure 9:
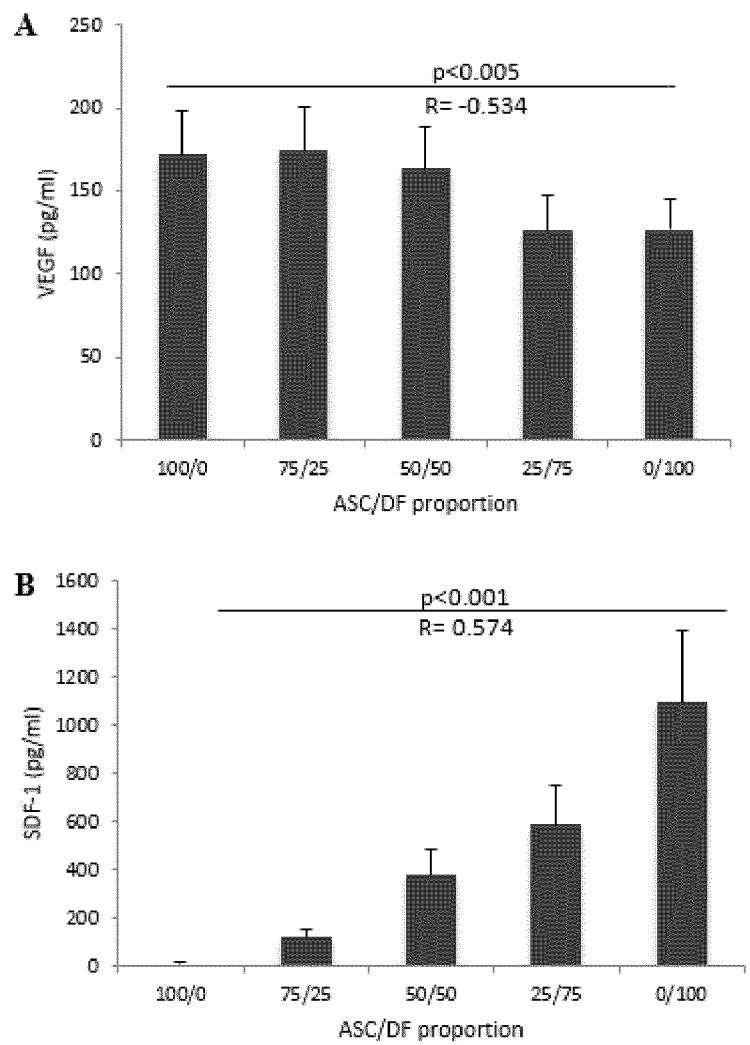
FIG. 9 is a set of histograms showing VEGF secretion (A) and SDF-1α secretion (B) of 5 different ASC/DF dilutions in proliferation medium with 1 g/l glucose, at 5% $O_2$.
Figure 10:
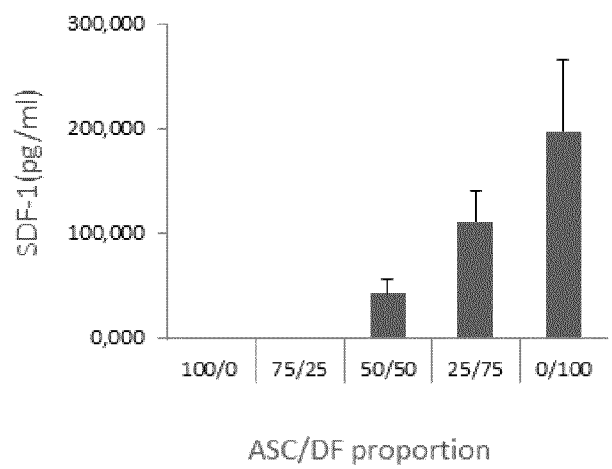
FIG. 10 is a histogram showing SDF-1α secretion of 5 different ASC/DF dilutions in proliferation medium with 1 g/l glucose, at 21% $O_2$.

However, for VEGF and SDF-1α, linear regressions following ASC "contamination" by DF were observed. Indeed, SDF-1α secretion level decreases with increasing ASC proportion. This result is found in different conditions of oxygen tension (21%, 5% or 0.1%) or of glucose concentrations (1 g/l or 4.5 g/l) (FIGS. 5 to 10). Moreover, in high glucose culture conditions and at 0.1% $O_2$ and 5% $O_2$ VEGF secretion level increases with increasing ASC proportion (FIGS. 5A and 6A). The same measurements in low glucose conditions demonstrated significant linear regressions for VEGF secretion at 5% $O_2$ (FIG. 8A).

The relations were inversed since DF release higher levels of SDF-1α and VEGF was produced in higher rates by ASC, allowing the measurement of the cell proportion (ASC purity).

The invention claimed is:

1. An in vitro method for preparing a substantially pure cell preparation of mesenchymal stem cells (MSCs) suitable for use as a cell therapy product in regenerative medicine, wherein said method comprises the steps of
   (i) providing a cell culture medium of a cell preparation comprising MSCs isolated from tissues,
   (ii) measuring the expression level of at least one growth factor secreted by said cell preparation into the cell culture medium, wherein said at least one growth factor is SDF-1 α and/or VEGF, and
   (iii) selecting the cell preparation as being substantially free of contaminating fibroblasts when the SDF-1α and/or VEGF expression levels are at least 80% of a reference expression level of SDF-1α and/or VEGF of a pure MSC preparation isolated from the same tissue and cultured in the same conditions as said cell preparation, wherein the SDF-1α expression level is at most 100 pg/ml and/or the VEGF expression level is at least 90 pg/ml, and wherein the expression levels are measured at the protein level,
   thereby preparing a substantially pure MSC preparation suitable for use as a cell therapy product in regenerative medicine.

2. The in vitro method according to claim 1, wherein said mesenchymal stem cells are isolated from tissues selected from the group consisting of adipose tissue, bone marrow, umbilical cord blood, amniotic fluid, Wharton's jelly, placenta, peripheral blood, fallopian tube, corneal stroma, lung, muscle, and fetal liver.

3. The in vitro method according to claim 1, wherein said mesenchymal stem cells are adipose stem cells (ASCs).

4. The in vitro method according to claim 1, wherein said cell preparation is selected as being substantially pure when the SDF-1α expression level is of at most 100 pg/ml and/or the VEGF expression level is of at least 200 pg/ml in the cell culture medium, and wherein said cell preparation is cultured in hypoxic conditions and at high concentration of glucose, before measuring the expression level.

5. The in vitro method according to claim 1, wherein said cell preparation is selected as being substantially pure when the SDF-1α expression level is of at most 100 pg/ml and/or the VEGF expression level is of at least 90 pg/ml in the cell culture medium, and wherein said cell preparation is cultured at tissular oxygen tension and at high concentration of glucose, before measuring the expression level.

6. The in vitro method according to claim 1, wherein said expression level is measured at the protein level and wherein said measure is the detection and/or quantification of said at least one growth factor secreted in the cell culture supernatant.

7. The in vitro method according to claim 4, wherein said cell preparation is cultured at about 0.1% O2 and at about 4.5 g/l of glucose, before measuring the expression level.

8. The in vitro method according to claim 5, wherein said cell preparation is cultured at about 5% O2 and at about 4.5 g/l of glucose, before measuring the expression level.

9. The in vitro method according to claim 4, wherein said cell preparation is selected as being substantially pure when the SDF-1α expression level is of at most 50, 40, 30, 25, 20, 19, 18, 17, 16, 15, 14, 13, 12, 11, 10, 9, 8, 7, 6, 5, 4, 3, 2 or 1 pg/ml; and/or the VEGF expression level is at least 250, 260, 270, 280, 281, 282, 283, 284, 285, 286, 287, 288, 289 or 290 pg/ml in the cell culture medium.

10. The in vitro method according to claim 5, wherein said cell preparation is selected as being substantially pure when the SDF-1α expression level is of at most 50, 40, 30, 25, 20, 19, 18, 17, 16, 15, 14, 13, 12, 11, 10, 9, 8, 7, 6, 5, 4, 3, 2 or 1 pg/ml; and/or the VEGF expression level is of at least 95, 100, 105, 110, 111, 112, 113, 114, 115, 116, 117, 118, 119 or 120 pg/ml in the cell culture medium.

11. The in vitro method according to claim 1, wherein said cell preparation of MSCs isolated from tissues are cultured in vitro for one or more passages prior to providing the cell culture medium for measuring the expression level of at least one growth factor.

* * * * *